(12) United States Patent
Takahashi et al.

(10) Patent No.: US 7,604,938 B2
(45) Date of Patent: Oct. 20, 2009

(54) DEVICES AND METHODS FOR MONITORING GENOMIC DNA OF ORGANISMS

(75) Inventors: Toru Takahashi, Tokyo (JP); Hiroshi Inoue, Bethesda, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 11/356,807

(22) Filed: Feb. 17, 2006

(65) Prior Publication Data

US 2006/0257893 A1 Nov. 16, 2006

Related U.S. Application Data

(60) Provisional application No. 60/653,978, filed on Feb. 18, 2005.

(51) Int. Cl.
*C12Q 1/68* (2006.01)
*C12M 1/00* (2006.01)
(52) U.S. Cl. .................................. 435/6; 435/283.1
(58) Field of Classification Search ................ 435/91.1, 435/91.2
See application file for complete search history.

(56) References Cited

U.S. PATENT DOCUMENTS

| | | | | |
|---|---|---|---|---|
| 5,736,314 | A * | 4/1998 | Hayes et al. ................... | 435/4 |
| 5,779,868 | A | 7/1998 | Parce et al. ................. | 204/604 |
| 5,800,690 | A | 9/1998 | Chow et al. ................. | 204/451 |
| 5,876,675 | A | 3/1999 | Kennedy ...................... | 422/99 |
| 5,882,465 | A | 3/1999 | McReynolds ............... | 156/285 |
| 5,965,410 | A | 10/1999 | Chow et al. ................. | 435/91.2 |
| 6,174,709 | B1 | 1/2001 | Kenten et al. .............. | 435/91.2 |
| 6,267,858 | B1 | 7/2001 | Parce et al. ................. | 204/600 |
| 6,337,212 | B1 | 1/2002 | Nagle et al. ................. | 436/174 |
| 6,379,974 | B1 | 4/2002 | Parce et al. ................. | 436/180 |
| 6,416,642 | B1 | 7/2002 | Alajoki et al. .............. | 204/451 |
| 6,465,257 | B1 | 10/2002 | Parce et al. ................. | 436/180 |
| 6,482,364 | B2 | 11/2002 | Parce et al. ................. | 422/100 |
| 6,495,369 | B1 | 12/2002 | Kercso et al. ............... | 436/47 |
| 6,500,323 | B1 | 12/2002 | Chow et al. ................. | 204/450 |
| 6,534,262 | B1 | 3/2003 | McKernan et al. ............ | 435/6 |
| 6,556,923 | B2 | 4/2003 | Gallagher et al. ............ | 702/23 |
| 6,558,944 | B1 | 5/2003 | Parce et al. .............. | 435/287.2 |
| 6,558,960 | B1 | 5/2003 | Parce et al. ................. | 436/519 |
| 6,582,576 | B1 | 6/2003 | Chow et al. ................. | 204/601 |
| 6,613,581 | B1 | 9/2003 | Wada et al. ................. | 436/518 |
| 6,670,153 | B2 | 12/2003 | Stern ........................ | 435/91.2 |
| 6,718,742 | B1 | 4/2004 | Baker ........................... | 54/28 |
| 6,752,966 | B1 | 6/2004 | Chazan ...................... | 422/102 |
| 6,852,524 | B2 | 2/2005 | Okamura et al. .......... | 435/287.1 |
| 2002/0197630 | A1 * | 12/2002 | Knapp et al. .................. | 435/6 |
| 2003/0054395 | A1 | 3/2003 | Baker ............................ | 435/6 |
| 2003/0104466 | A1 | 6/2003 | Knapp et al. .................. | 435/6 |
| 2003/0130499 | A1 | 7/2003 | Baker ....................... | 536/25.4 |
| 2004/0089548 | A1 | 5/2004 | Burd Mehta et al. ........ | 204/450 |
| 2004/0152076 | A1 | 8/2004 | Willson et al. ................. | 435/6 |
| 2004/0241651 | A1 | 12/2004 | Olek et al. ..................... | 35/6 |
| 2005/0009022 | A1 | 1/2005 | Weiner et al. ................. | 435/6 |

FOREIGN PATENT DOCUMENTS

| | | |
|---|---|---|
| EP | 1149921 A | 10/2001 |
| EP | 1 510 576 A1 | 3/2005 |
| JP | 2002-291500 | 10/2002 |
| JP | 2002-325581 | 11/2002 |
| JP | 2003-083965 | 3/2003 |
| JP | 2003-093075 | 4/2003 |
| JP | 2003-180351 | 7/2003 |
| JP | 2003-180374 | 7/2003 |
| JP | 2003-274959 | 9/2003 |
| JP | 2003-334082 | 11/2003 |
| JP | 2004-041191 | 2/2004 |
| JP | 2004-057202 A | 2/2004 |
| JP | 2004-185583 | 7/2004 |
| JP | 2004-236651 | 8/2004 |
| JP | 2004-361310 A | 12/2004 |

(Continued)

OTHER PUBLICATIONS

Kong et al. Journal of Clinical Microbiology, vol. 38, pp. 4256-4259, 2000.*

(Continued)

*Primary Examiner*—Gary Benzion
*Assistant Examiner*—Cynthia B Wilder
(74) *Attorney, Agent, or Firm*—Rothwell, Figg, Ernst & Manbeck

(57) ABSTRACT

The invention provides an apparatus that can be used in methods of preparing, amplifying, detecting, and/or optionally selecting for further analysis the genomic material from an organism for the rapid detection and/or classification of an organism in a sample (e.g., screening for, identifying, quantifying, and/or optionally further analyzing, e.g., sequencing, the genomic material of the organism). The invention further provides methods of using the apparatus, e.g., in combination with novel SGP primers for improved use in waveform-profiling methods of DNA amplification. It is an object of the invention to provide an apparatus for fully automated analysis of genomic material, and multiple methods of using the apparatus that are beneficial to society, e.g., the apparatus may be used in methods of screening for, identifying, quantifying, and/or selecting genomic material for further analysis (e.g., sequencing) in relation to monitoring a source for the presence of contaminating organisms.

34 Claims, 11 Drawing Sheets

FOREIGN PATENT DOCUMENTS

| | | |
|---|---|---|
| WO | WO 94/24307 A | 10/1994 |
| WO | WO 97/41219 | 11/1997 |
| WO | WO 99/12031 A | 3/1999 |
| WO | WO 99/16162 | 4/1999 |
| WO | WO 01/02850 A | 1/2001 |
| WO | WO 02/10373 A2 | 2/2002 |
| WO | WO 02/083952 A | 10/2002 |
| WO | WO 2004/090132 | 10/2004 |
| WO | WO 2004/104196 | 12/2004 |
| WO | WO 2005/003395 | 1/2005 |
| WO | WO 2005/005664 | 1/2005 |

OTHER PUBLICATIONS

Adgene Co., Ltd. "Goodbye DNA Chip, Hello Genopattern for 21$^{st}$ Century" (www.adgene.co.jp) (published at least as early as Oct. 17, 2003; pp. 1-8).

Adgene Co., Ltd. "A method for comparison and identification of DNAs and RNAs by pattern analysis: Genopattern Method" (www.adgene.co.jp) (published at least as early as Nov. 24, 2002; pp. 1-9).

Alberti and Mergny "DNA duplex-quadruplex exchange as the basis for a nanomolecular machine" *PNAS* 100(4)1569-73 (Feb. 2003).

Antolin et al. "Intensive Linkage Mapping in a Wasp (*Bracon hebetor*) and a Mosquito (*Aedes aegypti*) with Single-Strand Conformation Polymorphism Analysis of Random Amplified Polymorphic DNA Markers" *Genetics* 143:1727-38 (Aug. 1996).

Arnau et al. "The Use of RAPD Markers in the Genetic Analysis of the Plant Pathogenic Fungus *Cladosporium fulvum*" *Curr. Genet.* 25:438-44 (1994).

Butler "Nucleic acid sequence analysis software packages" *Curr. Opin. Biotechnol.* 5(1):19-23 (1994).

Burpo "A critical review of PCR primer design algorithms and cross-hybridization case study" Standford Computer Molecular Biology Course Materials (2001) (cmgm.stanford.edu/biochem218/Projects%202001/Burpo.pdf) (printed Apr. 12, 2007; pp. 1-11).

Cooksey et al. "Temperature-Mediated Heteroduplex Analysis Performed by Using Denaturing High-Performance Liquid Chromatography To Identify Sequence Polymorphisms in *Mycobacterium tuberculosis* Complex Organisms" *J. Clin. Microbiol.* 40:1610-16 (May 2002).

Constans "Nano-Quakes: Advalytix's programmable biochips shake up the lab-on-a-chip market" *The Scientist* 17(7):48 (Apr. 2003) (www.the-scientist.com/yr2003/apr/tools_030407.html) (printed Mar. 18, 2004; pp. 1-3).

Darby et al. "High throughput measurement of duplex, triplex and quadruplex melting curves using molecular beacons and a LightCycler" *Nucleic Acids Res.* 30(9):e39, 1-8 (May 2002).

Descheemaeker et al. "Evaluation of Arbitrarily Primed PCR Analysis and Pulsed-Field Gel Electrophoresis of Large Genomic DNA Fragments for Identification of Enterocci Important in Human Medicine" *Int J. Syst. Bacteriol.* 47(2):555-61 (Apr. 1997).

Holding "Lab on a Chip: Miniaturized microfluidic device analyzes multiple samples in parallel" *The Scientist* (Mar. 15, 2004) (www.biomedcentral.com/news/20040315/02) (printed Mar. 18, 2004; pp. 1-3).

Kemp "Capillary electrophoresis: a versatile family of analytical techniques" *Biotechnol. Appl. Biochem.* 27:9-17 (Feb. 1998).

Kopp et al. "Chemical amplification: continuous-flow PCR on a chip" *Science* 280:1046-48 (May 1998).

Kozwich et al. "Development of a Novel, Rapid Integrated *Crptosporidium parvum* Detection Assay" *Appl. Environ. Microbiol.* 66(7):2711-17 (Jul. 2000).

Marx "PCR-on-a-Chip Downsizes Even as It Grows Up" *Genomics & Proteomics* (www.genpromag.com/ShowPR_Print.aspx?PUBCODE=018&ACCT-1800000100~ISSUE~0404 ~ RELTYPE~PR~ORIGRELTYPE~GPF~PRODCODE~00000000~ PRODLETT~E=CALLFROM=RELPGM.html) (printed Jun. 7, 2007; pp. 1-4).

Naimuddin et al. "Commonly Conserved Genetic Fragments Revealed by Genome Profiling Can Serve as Tracers of Evolution" *Nucleic Acids Res.* 30(10):e42, 1-6 (May 2002).

"Melting Curve Technology" (Roche Diagnostics Corporation (2003)) (www.roche-applied-science.com/sis/lighttyper/It_frames/frame_technology.jsp) (printed Jun. 6, 2007; pp. 1-2).

Schwartz et al. "Detection of antibiotic-resistant bacteria and their resistance genes in wastewater, surface water, and drinking water biofilms," *FEMS Microbiol. Ecol.* 43:325-35 (2003) (first published online Nov. 23, 2002).

Sinclair "Small Wonder: Agilent Technologies and Caliper Technologies bring lab-on-a-chip technology to the research bench" *The Scientist* 14(5):25-27 (Mar. 2000) (www.the-scientist.com/yr2000/mar/profile_000306.html) (printed Mar. 18, 2004; pp. 1-3).

Swaminathan and Barrett "Amplification Methods for Epidemiologic Investigations of Infectious Diseases" *J. Microbiol. Meth.* 23:129-39 (1995).

Wang et al. "RAPD (Arbitrary Primer) PCR is More Sensitive than Multilocus Enzyme Electrophoresis for Distinguishing Related Bacterial Strains" *Nucleic Acids Res.* 21(25):5930-33 (1993).

Welsh and McClelland "Fingerprinting Genomes Using PCR With Arbitrary Primers" *Nucleic Acids Res.* 18(24):7213-18 (Dec. 1990).

"Geopattern Analyzer GP1000" (www.yamato-net.co.jp/english/products/bio/gp1000.htm) (printed May 21, 2007; pp. 1-8).

"PCR Primer Design" (www.premierbiosoft.com/tech_notes/PCR_Primer_Design.html) (printed Apr. 12, 2007; pp. 1-5).

Kong et al. "Rapid-cycle PCR for detection and typing of *Mycoplasma pneumoniae* in clinical specimens," J. Clin. Microbiol. (2000) 38/2:4256-59.

Williams et al. "DNA polymorphisms amplified by arbitrary primers are useful as genetic markers" *Nucleic Acids Res.* 18(22):6531-34 (1990).

\* cited by examiner

5' TCTTGCACTTTGGGTAACGCACGTGTGGCTGCGCTTCAAGTCATACCGCGAAC 3'
3' agaacgtgaaacccattgcgtgcacaccgacgcgaagttcagtatggcgcttg 5'

5' TATTATGCGCAGCCGACAGCAACTATCTGAACGAGCGAGGGCCATCAAGCCTG 3'
3' ataatacgcgtcggctgtcgttgatagacttgctcgctcccggtagttcggac 5'

5' GCATATCGTCAGGTCACCACGTGGGTGCAATGCGCGTCACTCTCTTCCACCCT 3'
3' cgtatagcagtccagtggtgcacccacgttacgcgcagtgagagaaggtggga 5'

5' TGTGTAATAATTGTACAAACATCCACTGTTCTCTCAGAGAACATATGTCCCG 3'
3' acacattattaacatgtttgtaggtgacaagagagtctcttgtatacaggggc 5'

5' GCGCTCTAAGTAACACCGGCAAAATTTTGA[AGCCCAAAGGGCCTTCGGCT]GC 3'
3' cgcgagattcattgtggccgttttaaaaact[tcgggtttcccggaagccg]cg 5'

5' CAACTCTCGGAGGATCGCCGTTCAACCGCCGGTAGAGACAGTATACAAATTAT 3'
3' gttgagagcctcctagcggcaagttggcggccatctctgtcatatgtttaata 5'

5' ACAGAGTCCTATGGCAGGATTGTTCTCCAGTATGCAACCGTGAGGCACGCCAG 3'
3' tgtctcaggataccgtcctaacaagaggtcatacgttggcactccgtgcggtc 5'

5' AAGCAGTCTGTCTTTCCTGGGACGTGAATTTGCTTTGATTGCATGCTCAGTAC 3'
3' ttcgtcagacagaaaggaccctgcacttaaacgaaactaacgtacgagtcatg 5'

5' GCGAGGCTTCTCCGCAAGATTCACAAAAGCAACGCGGTTTGCCAACGTAGGGA 3'
3' cgctccgaagaggcgttctaagtgttttcgttgcgccaaacggttgcatccct 5'

5' TTGAGACCAAATCCCATCGGTAATTGAGGCAAAGATTCCGCCAGCCATGGTAA 3'
3' aactctggtttagggtagccattaactccgtttctaaggcggtcggtaccatt 5'

5' ATTACCCTTCTACCTGGG[AGCT]AGCGATTGCGTGGACAAAGCGCATGTGCGA 3'
3' taatgggaagatggaccc[tcg]tcgctaacgcacctgtttcgcgtacacgct 5'

5' GCGGACGTTGGGCAGTCCAGAAAGAGGT[AGCGGGGCT]ATCTATTAGTAACGA 3'
3' cgcctgcaacccgtcaggtctttctcca[tcgccccg]agataatcattgct 5'

5' CATAGGAGGTCCGAGATAGGTACCCAATTTCTTTATATTGTTAGGGATTCCCC 3'
3' gtatcctccaggctctatccatgggttaaagaaatataacaatccctaagggg 5'

5' GTACTCCTTTTCAGGGGCCTAAGGACCCTTTCTTCCGACGTTTACTATACCT 3'
3' catgagaggaaagtccccggattcctgggaagaaggctgcaaatgatatgga 5'

5' AGCATGGTCTTAAGGGATCCATTTATCTGTATGTAGTATTACGTTGGTGCTGA 3'
3' tcgtaccagaattccctaggtaaatagacatacatcataatgcaaccacgact 5'

5' TCAGTTTATACTCCGCTGTGACCATCGTTAAGTATACCACCGGCTAACTCCGC 3'
3' agtcaaatatgaggcgacactggtagcaattcatatggtggccgattgaggcg 5'

5' GCTTATGGGGACTTATGGCTTCATGGCCCACTTACAAGATGGGTGAGTTCGT 3'
3' cgaataccccctgaataccgaagtaccgggtgaatgttctacccactcaagca 5'

5' GTTCCACCACCTGTCCGGGGTGCTGAGGCAGATGTGATCGTTGGTAGGCCCAA 3'
3' caaggtggtggacaggccccacgactccgtctacactagcaaccatccgggtt 5'

5' GTTC[AGCCGATGATGCCTTGCT]CCTCGCAGTAGATGCAGCACTCTTC 3'
3' caa[tcggctactacggaacga]ggagcgtcatctacgtcgtgagaag 5'

FIGURE 4

SEQ ID NO:2

| SGP nucleic acid polymers derived from the genomic DNA template set forth as SEQ ID NO:2 | SGP nucleic acid polymers derived from the genomic DNA template set forth as SEQ ID NO:1 |
|---|---|
| 5'-AGCCGAC-3' (SEQ ID NO:3) | 3'-aacccattgcgtgcacaccga-5' (SEQ ID NO:19) |
| 5'-AGCAACTATCTGAACG-3' (SEQ ID NO:4) | 3'-cgcga-5' (SEQ ID NO:20) |
| 5'-AGCGAGGGCCATCA-3' (SEQ ID NO:5) | 3'-tcttgtatacaggggccgcga-5' (SEQ ID NO:21) |
| 5'-AGCCTGGCATATCGTCAGGTC-3' (SEQ ID NO:6) | 3'-ttcgggtttcccggaagccga-5' (SEQ ID NO:22) |
| 5'-AGCCCAAAGGGCCTTCGGCTG-3' (SEQ ID NO:7) | 3'-aaggaccctgcacttaaacga-5' (SEQ ID NO:23) |
| 5'-AGCAGTCTGTCTTTCCTGGGA-3' (SEQ ID NO:8) | 3'-aactaacgtacga-5' (SEQ ID NO:24) |
| 5'-AGCAACGCGGTTTGCCAACGT-3' (SEQ ID NO:9) | 3'-gtcatgcgctccga-5' (SEQ ID NO:25) |
| 5'-AGCCATGGTAAATTACCCTTC-3' (SEQ ID NO:10) | 3'-atgggaagatggaccccctcga-5' (SEQ ID NO:26) |
| 5'-AGCT-3' (SEQ ID NO:11) | 3'-gtctttctccatcgcccccga-5' (SEQ ID NO:27) |
| 5'-AGCGATTGCGTGGACAA-3' (SEQ ID NO:12) | 3'-tacatcataatgcaaccacga-5' (SEQ ID NO:28) |
| 5'-AGCGCATGTGCG-3' (SEQ ID NO:13) | 3'-ctagtcaaatatgaggcga-5' (SEQ ID NO:29) |
| 5'-AGCGGACGTTGGGCAGTCCAG-3' (SEQ ID NO:14) | 3'-agcaattcatatggtggccga-5' (SEQ ID NO:30) |
| 5'-AGCGGGGGCTATCTATTAGTA-3' (SEQ ID NO:15) | 3'-ttgaggcgcga-5' (SEQ ID NO:31) |
| 5'-AGCATGGTCTTAAGGGATCCA-3' (SEQ ID NO:16) | 3'-atacccccctgaataccga-5' (SEQ ID NO:32) |
| 5'-AGCCGATGATGCCTTGCTCCT-3' (SEQ ID NO:17) | 3'-ggtggtggacaggccccacga-5' (SEQ ID NO:33) |
| 5'-AGCACTCTTC-3' (SEQ ID NO:18) | 3'-aagtcggctactacggaacga-5' (SEQ ID NO:34) |

FIGURE 7

| SGP-SGP nucleic acid polymers amplified from SGP nucleic acid polymers derived from the genomic DNA template set forth as SEQ ID NO:2 | SGP-SGP nucleic acid polymers amplified from SGP nucleic acid polymers derived from the genomic DNA template set forth as SEQ ID NO:1 |
|---|---|
| Not applicable | Not applicable |
| Not applicable | Not applicable |
| Not applicable | Not applicable |
| Not applicable | 5'-AGCCCAAAGGGCCTTCGGCT-3' (SEQ ID NO:39) |
| 3'-tcgggtttcccggaagccga-5' (SEQ ID NO:35) | Not applicable |
| Not applicable | Not applicable |
| Not applicable | Not applicable |
| Not applicable | 5'-AGCT-3' (SEQ ID NO:40) |
| 3'-tcga-5' (SEQ ID NO:36) | 5'-AGCGGGGGCT-3' (SEQ ID NO:41) |
| Not applicable | Not applicable |
| Not applicable | Not applicable |
| Not applicable | Not applicable |
| 3'-tcgccccga-5' (SEQ ID NO:37) | Not applicable |
| Not applicable | Not applicable |
| 3'-tcggctactacggaacga-5' (SEQ ID NO:38) | Not applicable |
| Not applicable | 5'-AGCCGATGATGCCTTGCT-3' (SEQ ID NO:42) |

FIGURE 8

| Shortened SGP nucleic acid polymers (underlined) elongated from SGP-SGP nucleic acid polymers amplified from SGP nucleic acid polymers derived from the genomic DNA template set forth as SEQ ID NO:2 | Shortened SGP nucleic acid polymers (underlined) elongated from SGP-SGP nucleic acid polymers amplified from SGP nucleic acid polymers derived from the genomic DNA template set forth as SEQ ID NO:1 |
|---|---|
| Not applicable | Not applicable |
| Not applicable | Not applicable |
| Not applicable | Not applicable |
| Not applicable | 3'-cggaagccga-5' (SEQ ID NO:47) |
| 5'-AGCCCAAAGG-3' (SEQ ID NO:43) | Not applicable |
| Not applicable | Not applicable |
| Not applicable | Not applicable |
| Not applicable | 3'-tcga-5' (SEQ ID NO:48) |
| 5'-AGCT-3' (SEQ ID NO:44) | 3'-tcgccccga-5' (SEQ ID NO:49) |
| Not applicable | Not applicable |
| Not applicable | Not applicable |
| Not applicable | Not applicable |
| 5'-AGCGGGGGCT-3' (SEQ ID NO:45) | Not applicable |
| Not applicable | Not applicable |
| 5'-AGCCGATGAT-3' (SEQ ID NO:46) | Not applicable |
| Not applicable | 3'-tacggaacga-5' (SEQ ID NO:50) |

DEVICES AND METHODS FOR MONITORING GENOMIC DNA OF ORGANISMS

RELATED APPLICATIONS

This application claims the benefit of priority from U.S. Provisional Patent Application No. 60/653,978, filed Feb. 18, 2005, which is hereby incorporated by reference herein in its entirety.

BACKGROUND OF THE INVENTION

1. Field of the Invention

This invention is directed to an apparatus that can be used in methods of preparing, amplifying, detecting, and/or optionally selecting for further analysis the genomic material from an organism for the rapid detection and/or classification of an organism in a sample (e.g., screening for, identifying, quantifying, and/or optionally further analyzing, e.g., sequencing, the genomic material of the organism).

2. Related Background Art

Recent basic and innovative developments have allowed biotechnological processes to become more sophisticated and simultaneously more complicated. For example, although many useful techniques have been developed to reduce the cost of, simplify, and standardize processes of DNA preparation, amplification, detection, and identification, there are no known apparatuses on the market that allow the full automation of these processes for the screening, quantification, identification, and/or further analysis, e.g., sequencing, of DNA.

In the biotechnological field, there is a need for rapid detection and/or classification of organisms, such as bacteria and viruses, in a variety of samples (e.g., environmental and medical). For example, rapid detection of bacteria, and subsequent classification of the species and/or strain, may be necessary to provide quality assurance for, e.g., a local water supply, a hospital, or a food processing plant; i.e., it may be necessary to monitor various samples, including but not limited to samples of air, dust, water, blood, tissues, plants, foodstuffs, etc., for the presence of contaminating organisms, and to classify the contaminating organisms prior to consumption, exposure, and/or use by the public, or during use by the public.

Standard microbiological methods for detecting and/or classifying an organism, e.g., culturing and Gram-staining or testing of other biochemical properties, are imprecise and often cannot differentiate among different organisms, let alone different strains of an organism. More precise methods for detecting and/or identifying an organism are based on the genomic DNA of the organism. One such well-known method of detection and/or identification (classification) is the polymerase chain reaction (PCR), for which technological developments have increased its level of throughput and automation.

PCR is effectuated by two separate and distinct (first and second) primers, each of which is respectively complementary to a nucleotide sequence found on either of the two templates of the genomic DNA. Since the sequences of the two primers are based on the sequences of the two genomic DNA templates, the two primers bind to and bracket a singular and isolated locus of the double-stranded genomic DNA. PCR using such a pair of primers results in the exponential amplification of double-stranded genomic DNA that is identical to the singular and isolated locus of the genome bracketed by nucleotide sequences complementary to the two primers, i.e., a locus of DNA flanked by a first primer binding site on the 3'-end of one genomic DNA template and a second primer binding site on the 3'-end of the other genomic DNA template.

PCR is useful in detecting small amounts of DNA, not only because it results in the exponential amplification of double-stranded DNA, but also because of the development of new technologies that increase the level of PCR throughput and automation. An example of one such technology is the use of microfluidic systems, including controller/detector interfaces for microfluidic devices, as described in, e.g., U.S. Pat. Nos. 6,500,323 and 6,670,153. These microfluidic systems, collectively referred to herein as automated inline PCR platforms, are well known in the art and are generally described below.

Most automated inline PCR platforms utilize a microfluidic chip that works with controller/detector interfaces for automated sample accession, microfluidic PCR reagent assembly, PCR thermal cycling, and optical detection spectroscopy. A microfluidic chip generally comprises a first plate with at least one micro-etched fluidic (microfluidic) inline reaction channel that may be bonded to a second plate, within which may be metal traces and a fluid reservoir. When the two plates are bonded together to form the microfluidic chip, each microfluidic reaction channel of the first plate may connect with a fluid reservoir of the second plate so that locus-specific reagents can be delivered through the fluid reservoirs to the microfluidic inline reaction channels.

Usually, automated inline PCR using a microfluidic chip does not occur in a chamber; instead, the reaction occurs as the sample is moved along and inside a microfluidic inline reaction channel. Inline PCR begins when a capillary, or "sipper," aspirates a sample droplet (which may or may not be a DNA sample droplet, i.e., a sample droplet comprising genomic material isolated from an organism) from, e.g., a microtiter plate (which may come from, e.g., a robotic handler) into at least one microfluidic inline reaction channel. After aspirating a sample droplet into a microfluidic inline reaction channel, the sipper can be moved to a buffer trough so that buffer is drawn into the microfluidic chip. Consequently, cross-contamination among sample droplets is minimized since each sample droplet is separated from adjacent sample droplets by buffer spacers. Each sample droplet is then moved along a microfluidic inline reaction channel and into a PCR assembly area of the chip, wherein the sample droplet becomes a sample plug by being mixed with PCR-required reagents, e.g., a primer pair, DNA polymerase, and dNTPs, and detectable agents, e.g., intercalators, etc. Optionally, buffer spacers may also be mixed with PCR-required reagents to serve as negative controls. After being mixed with PCR-required and detectable agents, a sample plug (which may or may not be a DNA sample plug, i.e., a sample plug comprising genomic material) is moved along the length of the microfluidic inline reaction channel into different areas of the chip, e.g., an amplification area wherein PCR may be effected on the sample plugs.

Generally, as each sample plug (e.g., a DNA sample plug) flows through a microfluidic inline reaction channel, it enters an amplification area, i.e., a temperature-controlled area, wherein each microfluidic inline reaction channel is repeatedly and rapidly heated and cooled in a localized manner such that the denaturing, annealing and elongation steps of PCR are effected on each sample plug as it moves through the channel. A skilled artisan will recognize that amplification of DNA will occur only in DNA sample plugs, i.e., sample plugs comprising genomic material. A method of controlling the temperature in the amplification area is Joule heating (see, e.g., U.S. Pat. Nos. 5,965,410 and 6,670,153). Generally, voltage can be applied to the metal traces in a controlled and localized manner to effectuate the different temperatures required for each cycle of PCR (i.e., each cycle of denaturing, annealing, and elongation). Cooling of the reaction can be achieved through the use of, e.g., cooling fluid that travels through a coil to carry away thermal energy in the form of heat from the microfluidic inline reaction channel, or by allowing rapid heat dissipation, e.g., via the application of cold water to the bottom surface of the microfluidic chip. Since the volume of fluid in the microfluidic channels is small and the metal traces are located very close to the microfluidic inline reaction channels, heating and cooling of the fluid in the channels (and hence, sample plugs) is accomplished very rapidly. Consequently, DNA sample plugs undergo PCR, and PCR cycles run such that, e.g., 30 cycles may be performed in less than nine minutes. The number of PCR cycles each DNA sample plug sees as it travels through a microfluidic channel in the temperature-controlled area of the chip may be varied by changing either or both 1) the timing of the voltage applied to the metal traces, and 2) the flow rate of the DNA sample plugs through the microfluidic channels.

A microfluidic chip can simultaneously perform as many polymerase chain reactions as it has microfluidic inline reaction channels. For example, a sample comprising genomic material may be aspirated into multiple different microfluidic inline reaction channels, to each of which is added a different locus-specific reagent (e.g., a different primer pair that brackets a different locus on the genomic material, e.g., DNA). This allows for the simultaneous detection of several different loci on, e.g., genomic material isolated from the same organism. Alternatively, reagents comprising one specific primer pair may be aspirated into multiple different microfluidic inline reaction channels. This allows for the simultaneous detection of the same locus, e.g., on genomic material isolated from different organisms. Additionally, multiple sample droplets may be aspirated into the same microfluidic reaction channel.

A detection area is usually downstream of the temperature-controlled amplification area, and is generally a transparent region that allows observation and detection of the amplified DNA products, e.g., PCR products. In the detection area, each microfluidic inline reaction channel is usually brought in close proximity and passed under a detector. A light source is spread across the microfluidic inline reaction channels so that detectable agents, e.g., fluorescence emitted from each channel, e.g., from each DNA sample plug, passing through the optical detection area may be measured simultaneously. After the detection area, each microfluidic inline reaction channel usually leads each sample plug to a waste well.

Three different methods are usually used to generate fluid motion within microfluidic inline reaction channels; the methods involve electrokinetics, pressure, or a hybrid of the two (see, e.g., U.S. Pat. No. 6,670,153). In a pressure-based flow system, an internal or external source may be used to drive the flow of fluid in the inline reaction channels. For example, a vacuum may be applied to waste wells at the ends of each microfluidic inline reaction channel and may be used to activate the sipper and move the fluid along the microfluidic inline reaction channels toward the waste wells. Alternatively, since genomic material is charged, electrokinetics, i.e., the generation of a voltage gradient (e.g., by the application of voltage to the metal traces) may be used to drive charged fluid along the microfluidic inline reaction channels. A third method of driving the fluid along the inline reaction channels uses both electrokinetics and pressure. The result is a continuous flow of fluid within the microfluidic inline reaction channels, wherein sample plugs (e.g., DNA sample plugs) are continuously being mixed or moved to different areas (e.g., a PCR assembly area, a temperature-controlled area, a detection area, etc.) of the chip.

Electrokinetic and/or pressure-driven fluid movement, heating and cooling cycles, detection, and the data acquisition related to a microfluidic chip may be controlled by an instrument that interfaces at or with the chip (generally described in, e.g., U.S. Pat. No. 6,582,576). The interface of the instrument usually contains o-ring seals that seal the reagent wells on the chip, pogo pins that may interface with the metal traces on the chip and supply the voltage for temperature cycling, o-ring seals for the waste wells where a vacuum may be applied to move the fluid through the chip, a large o-ring that may be used to seal the bottom of the chip against circulating cool water and to speed the cooling during the temperature cycling, and a detection zone for, e.g., fluorescence detection. A skilled artisan will recognize that the risk of contamination with this system is minimal because a microfluidic chip is usually a closed system, physical barriers (e.g., buffer spacers) separate sample plugs (e.g., DNA sample plugs), and the continuous flow prevents sample plugs from moving backwards.

Since PCR (and consequently, automated inline PCR platforms) exponentially amplifies DNA, it may be used to detect small amounts of genomic material. However, because PCR requires primers that are specifically complimentary to sequences of the genomic material that are known and bracket the locus of interest, it is limited in that it can only be used for the detection and classification of known organisms. In other words, the investigator is required to know or guess the identity of the organism (i.e., the appropriate pair of primers to use) prior to any attempts at detecting the organism. Another limitation of PCR (and consequently of automated inline PCR platforms) is the inability of the investigator to obtain sequence information about the amplified DNA, other than information about the sequences complimentary to the two primers used in the analysis. Additionally, an automated inline PCR platform does not provide a means to further analyze, e.g., sequence, the genomic material in, e.g., a DNA sample plug, after it has traveled the length of a microfluidic inline reaction channel. Further analysis, e.g., providing the sequence, of the genomic material may be important and useful in, e.g., distinguishing a pathogenic strain from a non-pathogenic strain, detecting and providing the sequence of a new strain, etc.

To overcome some of the limitations of PCR, methods of waveform profiling were developed (see, e.g., the method of waveform profiling described in Japanese Patent Application Publication Nos. 2003-334082 and 2003-180351). Waveform profiling methods, e.g., those described in Japanese Patent Application Publication Nos. 2003-334082 and 2003-180351, provide ways to analyze and profile genomic material, e.g., DNA isolated from organisms, such as bacteria, without requiring the investigator to know or guess the identity of the organism prior to detection. Briefly, waveform profiling generally analyzes the genomic DNA of the organism using a unique primer(s) and the two denatured strands of the genomic DNA as templates to linearly amplify several distinct single-stranded nucleic acid polymers that form higher-order structures, e.g., triplexes, tetraplexes (or quadruplexes), etc. Because the genomic DNA of the organism is used as the template, the resulting single-stranded nucleic acid polymers will be distinct and contain sequences unique to the organism. Thus, the single-stranded nucleic acid polymers will form higher-order structures based on sequences unique to the organism. Accordingly, detection of such unique higher-order structures, which may be accomplished using detectable agents, e.g., fluorescent intercalators, may identify the organism.

The several distinct single-stranded nucleic acid polymers are usually produced using a single pattern generative waveform primer characterized by its structure and length. A waveform primer (i.e., a waveform-profiling primer) generally consists of two portions, a nonspecific stabilizing portion and a specific portion. As discussed below, the nonspecific stabilizing portion may help guide the formation of higher-order structures. In contrast, the specific portion guides the waveform primer to specifically bind to sequences complementary to its own sequence. The length of the waveform primer (e.g., 8-30 bases in length) is usually critical because it allows the specific portion of the primer to bind specifically to several discrete primer binding sites, i.e., sequences complementary to the waveform primer, along the length of a genomic DNA template. The binding of waveform primers to several primer-binding sites along each single-stranded genomic DNA template allows for the generation of several distinct single-stranded nucleic acid polymers, the generation of which is usually critical to this method.

In addition to utilizing a waveform primer, this method of waveform profiling also utilizes several cycles of linear amplification to provide multiple copies of each of several distinct single-stranded nucleic acid polymers; therefore, many copies of the waveform primer are added to a solution containing the genomic DNA of interest prior to the first cycle of linear amplification. Similar (at least generally) to PCR, one cycle of linear amplification comprises the following steps: 1) denaturing each copy of the double-stranded genomic DNA into two single-stranded genomic DNA templates, 2) annealing (i.e., providing conditions that allow the binding of) the waveform primer to several discrete primer binding sites on each single-stranded genomic DNA template, and 3) elongating several distinct single-stranded nucleic acid polymers from each of several waveform primers bound to primer binding sites along each genomic DNA template.

During one cycle of linear amplification, the temperature of the genomic DNA is increased (e.g., to 95-98° C.) to denature each copy of the genomic DNA into two single-stranded genomic DNA templates. The temperature is subsequently decreased (e.g., to 25° C.) to allow waveform primers to bind to several discrete primer-binding sites along the length of each denatured genomic DNA template. The final step in the cycle, elongation of several distinct single-stranded nucleic acid polymers from each bound waveform primer, is performed at ~72° C. using a polymerase, e.g., Taq polymerase. After this final step, the cycle repeats.

During the next denaturing step, the several distinct nucleic acid polymers are denatured from the genomic DNA templates and become single-stranded nucleic acid polymers, wherein each single-stranded nucleic acid polymer has a 5'-to-3' nucleotide sequence comprising the nucleotide sequence of the waveform primer from which the single-stranded nucleic acid polymer was elongated, followed by a distinct nucleotide sequence that is complementary to the sequence of the region of the genomic DNA template that was downstream of the genomic DNA sequence that bound to a waveform primer. Since each single-stranded nucleic acid polymer comprises the sequence of the waveform primer at its 5'-end, each single-stranded nucleic acid polymer also comprises the nonspecific stabilizing portion of the waveform primer. The nonspecific stabilizing portion of the waveform primer generally guides each single-stranded nucleic acid polymer to form higher-order structures and effectively prevents the single-stranded nucleic acid polymers from binding to any waveform primer in subsequent cycles of amplification.

In other words, the single-stranded nucleic acid polymers are not used as templates in subsequent cycles of amplification, and each cycle of amplification in this method of waveform profiling is linear and not exponential, i.e., each cycle of amplification produces only a single copy of each of the several distinct single-stranded nucleic acid polymers containing sequences unique to the organism, i.e., sequences complementary to sequences of the genomic DNA template that are downstream of waveform primers bound to primer binding sites. Thus, in contrast to PCR, which results in exponential amplification, waveform-profiling methods generally result in linear amplification, i.e., nonexponential amplification, of the several distinct single-stranded nucleic acid polymers containing sequences unique to the organism.

Each single-stranded nucleic acid polymer contains a base sequence complementary to a sequence of a genomic DNA template that is downstream of a waveform primer bound to a primer-binding site, so differences in base sequences present on multiple sites of different genomic DNAs may be compared and distinguished. As described above, the multiple copies of each of several distinct single-stranded nucleic acid polymers will interact with each other to form higher-order structures, i.e., complexes (e.g., triplexes and tetraplexes) comprising one or more single-stranded distinct nucleic acid polymers. The higher-order nucleic acid structures will have different stabilities and dissociate at different melting temperatures (Tm) depending on the base sequences of single-stranded nucleic acid polymers, i.e., based on the unique genomic information of the organism.

Waveform profiling generally requires that the Tm of the various different higher-order structures, produced using the genomic DNA of a particular organism as a template, be determined and recorded (melting temperature analysis); this can be accomplished with the use of fluorescent agents that intercalate into higher-order DNA structures, i.e., intercalators. The higher-order DNA structures generated by waveform profiling may be dissociated by increasing the temperature of the sample. As the higher-order DNA structures dissociate, the fluorescent agents intercalated in these higher-order structures will also dissociate. Plotting the rate of change of fluorescence intensity obtained by the dissociation of these higher-order structures as a function of increasing temperature will produce a waveform that is unique to the genomic DNA of the organism and the utilized waveform primer, i.e., the dissociation of higher-order DNA structures at different melting temperatures (Tm) are observed and recorded to produce a characteristic "waveform profile" for each species (or strain) of organism, e.g., bacteria. Thus, waveform profiling may be used to distinguish between genomic DNA isolated from a first organism and genomic DNA isolated from a second organism using melting temperature analysis and intercalators to obtain a unique waveform profile for each organism.

Since the above-described method (related to waveform profiling) relies on linear amplification, one of the difficulties of using this method is the requirement for a large starting amount of genomic DNA from the particular organism (e.g., bacteria) to be detected and/or identified. Consequently, waveform-profiling methods may be used to detect and identify organisms only if the organisms are present in large numbers (e.g., $10^6$ or more organisms) within a given sample, but are not effective for detecting and/or identifying a very small number of organisms. Additionally, similar to PCR, another limitation of this method is its inability to provide detailed information about the genomic material, e.g., sequence information.

Accordingly, waveform profiling methods are generally not useful in detecting and/or identifying an organism present in small numbers, e.g., in a sample taken from a water supply or source at the onset of contamination, or providing detailed information, e.g., sequence information, about the genomic material of the organism. Although PCR (and consequently, inline automated PCR platforms) may resolve the limitation of this waveform profiling method that requires a large starting sample (since PCR results in the exponential amplification of the genomic DNA and allows for the detection of organisms present in small numbers), it is known in the art that waveform profiles produced using the complementary double-stranded pieces of DNA that result from PCR amplification are insufficient for identification of particular genomic sequences (see, e.g., "Goodbye DNA Chip, Hello Genopattern for $21^{st}$ Century," printed and distributed by Adgene Co., Ltd.). Also, to date, there is no known automated inline PCR platform capable of detecting waveform profiles. In other words, the prior art not only explicitly teaches it is not possible to compare, differentiate and identify genomic material (from various species or strains of organisms) using melting temperature (Tm) analysis of standard PCR products, it also fails to provide technology that increases the levels of waveform profiling throughput and automation.

Additionally, although waveform profiling methods may provide for the rapid detection and/or classification of an organism via detection of its genomic DNA, these methods, as well as methods of PCR and inline automated PCR platforms, are all limited because they do not provide detailed information on the genomic material, e.g., sequence information, as provided by a sequencing chip (see, e.g., U.S. Published Patent Application No. 2005/0009022). Further examination of the genomic material, e.g., analysis of the sequence information, may be important, for example, when genomic variations among different strains of the same organism (which may be undetectable using, e.g., a particular PCR primer pair or waveform primer) cause the different strains to have different pathogenic properties, in the detection of new strains of infectious agents (e.g., variants of influenza virus or variants of a biological weapon), which may pose greater threats to public health, etc.

As described above, many basic methods (e.g., PCR, waveform profiling, etc.) and innovative technological developments (e.g., automated inline PCR platforms) have taken place in the field of detecting and/or classifying organisms. Although these methods and developments are becoming more sophisticated, and have simplified, standardized, and made more efficient the detection and/or classification of organisms, the present inventors know of no art-recognized apparatus that provides for the automation of all of these methods and developments simultaneously, i.e., an automated inline platform that allows for PCR, waveform profiling, and/or optionally selecting genomic material for further analysis, e.g., sequencing. The present invention overcomes this limitation by providing such an apparatus comprising microfluidic devices that may be used to detect and/or classify (e.g., screen for, quantify, identify, and/or optionally select for further analysis, e.g., sequencing of) genomic material (isolated from an organism (e.g., bacteria or viruses)) in a sample by automated methods of preparing (e.g., isolating, processing, mixing with reaction reagents, etc.), amplifying (e.g., by PCR, waveform profiling, etc.), detecting and/or optionally selecting for further analysis, e.g., sequencing.

SUMMARY OF THE INVENTION

It is an object of the present invention to provide an apparatus for fully automated analysis of genomic material, i.e., preparing (e.g., isolating, processing, mixing with reaction reagents, etc.), amplifying (e.g., by methods of PCR and/or waveform profiling), detecting (i.e., screening for, identifying, and/or quantifying), and optionally, selecting for further analysis of the genomic material. It is another object of the present invention to provide multiple methods of using the apparatus that are beneficial to society, e.g., the apparatus may be used in methods of screening for, identifying, quantifying, and/or selecting genomic material for further analysis, e.g., sequencing.

Screening a sample and detecting any unknown and potentially contaminating organism is an important and first method of using an apparatus of the invention, especially as a continuous (i.e., 24 hours a day, 7 days a week, and 365 days a year) measure, for example, as an anti-terrorism measure, to watch over and keep safe public supplies, e.g., water and air supplies. Since public supplies, e.g., water supplies, are expected to be safe, continuous screening of such supplies may result in constant acquisition of negative data, e.g., zero detection of contamination, rendering continuous screening expensive and seemingly redundant. A benefit of using an apparatus of the invention for the detection of the absence or presence of genomic material (i.e., contamination) is its relatively low cost associated with continuous screening.

Identification is another method of using an apparatus of the invention and is common in the analysis of genomic material. Because the apparatus of the invention may be used in methods detecting amplified DNA products generated by a known primer and/or that form a profile based on the genomic material of an organism, methods of using an apparatus of the invention for detection of the absence or presence of genomic material allow for the simultaneous identification of the organism from which the genomic material was isolated. Additionally, detecting the absence or presence of amplified products using an apparatus and methods of the invention will allow for the identification of whether more than one contaminating organism is present in the sample.

In another embodiment, an apparatus of the invention is used in methods of quantifying the amount of genomic material present in a sample. Such quantification may be useful for a deeper analysis in measuring, e.g., the progression of disease, the numerical differences in the presence or absence of a first and second organism, etc.

The ability to select genomic material for further analysis, e.g., sequencing, is a final (optional) method of the invention. A skilled artisan will recognize that further analysis may be required when the results from the detection, identification, and/or quantification methods of the invention suggest that a contaminating organism poses a serious threat.

It is another object of the invention to also provide an improved method of waveform profiling genomic material, which has been isolated from an organism(s) in a sample, even if the organism(s) is present in a small number in the sample. The improved waveform profiling method may be used with an apparatus of the invention.

Thus, the present invention provides an apparatus that allows automated inline detection of genomic material amplified via PCR and/or waveform profiling (including the improved methods of waveform profiling of the invention), and also provides the option to subsequently select for further analysis, e.g., sequencing of the detected genomic material.

In particular, the present invention is directed toward microfluidic systems, i.e., inline automated platforms, capable of producing and detecting amplified DNA products generated by waveform profiling methods.

The microfluidic systems, described herein, result in a novel inline automated platform that may be used with methods of either or both PCR and waveform profiling, and optionally, other methods of DNA analysis, e.g., sequencing methods. The invention also provides novel improvements to waveform profiling methods such that a modified version of PCR may be incorporated to allow the waveform profiling of a small starting amount of genomic material. Additionally, the present invention provides methods of using the inline automated platform of the invention, i.e., the apparatus comprising devices provided herein, to prepare, amplify, detect (e.g., screen for, quantify, identify), and/or optionally select for further analysis (e.g., sequence) genomic material isolated from an organism in a sample. One of skill in the art will recognize that the automated inline platform of the invention, the improved waveform profiling method, and the disclosed methods of using the automated inline platform of the invention (e.g., with the improved waveform profiling method) will allow for continuous detection, (e.g., screening, identification, quantification), and/or selection for further analysis (e.g., sequencing) of genomic material from an organism, even if the organism is present in a small number, e.g., the number of organisms present in a sample at the onset of contamination of a water supply or other source.

As such, the invention is directed toward microfluidic devices to allow for the detection of amplified DNA products (e.g., PCR-amplified products, higher order structures of waveform profiles, etc.) and to enable the detected DNA to be optionally selected for further analysis, e.g., by sequence analysis. In one embodiment of the invention, an inline automated microfluidic device of the invention comprises microfluidic inline reaction channel(s) that are within a second temperature-controlled area as they enter the detection area of the device. Placement of the microfluidic reaction channels in such a second temperature-controlled area allows for the detection of not only PCR amplified products, but also the detection of higher-order nucleic acid polymers generated with the waveform profiling methods (or improved methods thereof, as explained herein and in U.S. Provisional Patent Application No. 60/591,596, herein incorporated by reference) as the higher-order nucleic acid structures dissociate at different melting temperatures within the second temperature-controlled area, i.e., allowing for melting temperature analysis.

As such the present invention provides a microfluidic device comprising at least one sipper, at least one fluid reservoir connected to at least one microfluidic inline reaction channel, wherein the at least one microfluidic inline reaction channel runs through a reagent assembly area, an amplification area within a first temperature-controlled area, and a detection area within a second temperature-controlled area, and at least one metal trace for heating of and/or fluid movement within the microfluidic inline reaction channel, wherein detection of amplified DNA products may occur at more than one temperature (i.e., detection occurs at one or more temperatures).

In another embodiment of the invention, a microfluidic channel comprises a "valve" downstream of the detection area, such that a decision may be made regarding whether the DNA sample plug passing through the "valve" will be aspirated, e.g., into a waste well, or selected for further analysis, e.g., with a DNA sequencing chip.

As such the present invention provides a microfluidic device, comprising at least one sipper, at least one fluid reservoir connected to at least one microfluidic inline reaction channel, wherein the at least one microfluidic inline reaction channel runs through a reagent assembly area, an amplification area, and a detection area, and wherein the at least one microfluidic inline reaction channel further comprises a valve downstream of the detection area; and at least one metal trace for heating of and/or fluid movement within the microfluidic inline reaction channel.

The invention also provides a microfluidic device, comprising at least one sipper, at least one fluid reservoir connected to at least one microfluidic inline reaction channel, wherein the at least one microfluidic inline reaction channel runs through a reagent assembly area, an amplification area within a first temperature-controlled area, and a detection area within a second temperature-controlled area, and wherein the at least one microfluidic inline reaction channel further comprises a valve downstream of the detection area, and at least one metal trace for heating of and/or fluid movement within the microfluidic inline reaction channel, wherein detection of amplified DNA products may occur at more than one temperature.

Additionally, the present invention is directed to instruments (i.e., controllers/detectors), capable of controlling the fluid movement in the microfluidic devices of the invention, heating and cooling of the first and second temperature-controlled areas of microfluidic devices of the invention, and acquiring data from the microfluidic devices of the invention. As such, the present invention provides an instrument that controls fluid movement within, heating and cooling of, and data acquisition from, a microfluidic device of the invention comprising a cartridge that interfaces between the instrument and a microfluidic device of the invention. In one embodiment, the instrument establishes, monitors, controls and detects amplified products within a second temperature-controlled area. In another embodiment of the invention, the instrument is capable of deciding whether a sample plug at a valve will be directed toward a waste well or selected for further analysis, e.g., sequencing.

One of skill in the art will recognize that the devices and instruments described above will be useful not only in high throughput automated inline PCR, but also high throughput automated inline waveform profiling and/or optionally further methods of analysis, e.g., DNA sequencing.

The microfluidic devices and instruments of the invention are intended to work together to provide an automated inline platform for either or both PCR and waveform profiling methods and optionally, e.g., sequencing analysis. As such, the invention also provides an apparatus comprising a microfluidic device of the invention and an instrument of the invention. In addition, the apparatus may further comprise a cartridge that interfaces between the instrument and a microfluidic device of the invention; such cartridges are well known in the art.

Additionally, the invention is directed to improved methods of waveform profiling, collectively referred to herein as Single Genome Profiling (SGP). SGP requires the use of primers ("SGP primers") for the amplification of several distinct "SGP nucleic acid polymers." SGP primers are characterized by their length and ability to bind specifically to several discrete sites along the length of the genomic DNA. Since an SGP primer does not comprise a nonspecific stabilizing portion, SGP nucleic acid polymers (elongated from the SGP primers of the invention bound to several discrete SGP primer binding sites on, e.g., a single-stranded genomic DNA template) are free to bind SGP primers in subsequent amplification reactions. Because SGP primers may bind specifically to complementary nucleotide sequences along the length of single-stranded SGP nucleic acid polymers, an SGP primer also functions as both a forward and reverse primer (in a modified version of PCR, i.e., "mPCR") to allow the amplification of several distinct "SGP-SGP nucleic acid polymers," each of which comprises a nucleotide sequence identical to the sequence of one of several regions of genomic DNA that are bracketed by SGP primer binding sites, i.e., each SGP-SGP nucleic acid polymer sequence has at its 5'-end the sequence of the SGP primer and at its 3'-end the reverse complement of the SGP primer. Consequently, amplification of the several distinct SGP-SGP nucleic acid polymers comprising a nucleotide sequence of the SGP primer and the reverse complement sequence of the SGP primer occurs in an exponential (nonlinear) fashion, and enables using the present invention to detect and identify (classify) the genomic DNA of an organism, even if the organism is present in a small number. One of skill in the art will recognize that in practicing the present invention on RNA-based genomes (e.g., that of a retrovirus), a reverse transcription reaction should be performed prior to beginning SGP and the associated mPCR cycles.

The invention also provides a "half-time elongation step" associated with the final amplification step. In the present invention, the length of time for the elongation step associated with the final amplification step comprises a decrease in time (preferably the decrease in the length of time is approximately 40-60%; more preferably the decrease in the length of time is approximately 50%) resulting in a "half-time" elongation step in a final amplification cycle. Such a half-time elongation step typically will eliminate the exponential amplification of many SGP-SGP nucleic acid polymers because there will be insufficient time for elongation of the nucleic acid polymer from the SGP primer to the reverse complement of the SGP primer. Thus, shortened versions of SGP nucleic acid polymers ("shortened SGP nucleic acid polymers") will be produced from SGP-SGP nucleic acid polymers in the half-time step. One of skill in the art will recognize that, by performing the half-time elongation step subsequent to several cycles of exponential amplification with the modified version of PCR, i.e., mPCR, many copies of each of the shortened SGP nucleic acid polymers may be produced. Additionally, during a subsequent denaturing step, the shortened SGP nucleic acid polymers will become single-stranded. Ultimately, the shortened single-stranded SGP nucleic acid polymers form the higher-order structures that are detected in practicing the present invention with mPCR.

The present invention also provides the primers used in the improved methods, and methods for making these primers, as well as methods that utilize the exponential amplification and reduce the variability of waveform profiling method.

The present invention also provides methods for the continuous monitoring of a sample, or series of samples, for the absence or presence of a contaminating organism, and the subsequent and optional classification of the contaminating organism. In the methods of the invention, the automatic inline platform of the invention is used to prepare (e.g., isolate, process, mix with reaction reagents, etc.), amplify (e.g., by PCR, waveform profiling, etc.), and detect (e.g., screen for, identify, quantify), and/or optionally select for further analysis, e.g., sequence, genomic material isolated from an organism. Generally, methods of using an apparatus of the invention comprise the steps of isolating genomic material from an organism, if present, in a sample, aspirating sample droplets from the sample with a sipper into a microfluidic inline reaction channel of a microfluidic device of the invention, and forming sample plugs by mixing sample droplets with primer plugs. The sample plugs then flow along the microfluidic inline reaction channel into the amplification area of the microfluidic device of the invention, i.e., a first temperature-controlled area, wherein the sample plugs are subject to at least one amplification cycle comprising denaturing, annealing, and elongation. The sample plugs then enter the detection area of the microfluidic device of the invention, which may also be a second temperature-controlled area. In embodiments using waveform profiling, this detection area is also a second temperature-controlled area such that it allows each amplified DNA sample plug to be brought from a first temperature to a second temperature as the detectable agents of each sample plug are detected at temperatures ranging between the first and second temperatures. In some embodiments of the invention, a sample plug is surrounded by an immiscible nonaqueous fluid (e.g., mineral oil) as it is being aspirated to further prevent contamination (e.g., cross-contamination).

Thus, in one embodiment, the invention provides a method of determining an organism in a sample, the method comprising the steps of (a) acquiring the sample; (b) isolating at least one copy of the genomic DNA of the organism, if present in the sample; (c) introducing a first mixture comprising SGP primers, nucleotides, DNA polymerase, and intercalators to the genomic DNA of the organism to form a second mixture; (d) heating the second mixture to a first temperature that will cause the genomic DNA, if present, to denature into a first and second genomic DNA template; (e) cooling the second mixture to a second temperature that will cause the primers to anneal to each genomic DNA template; (f) reheating the second mixture to a third temperature that is between the first and second temperatures to allow the primers to remain annealed to the genomic DNA and the DNA polymerase to elongate nucleic acid polymers originating from the annealed primers; (g) maintaining the third temperature for a first length of time; (h) repeating steps (d)-(g) at least once; (i) repeating steps (d)-(f); (j) maintaining the third temperature for a second length of time equal to about 40-60% of the first length of time; (k) recooling the second mixture to a fourth temperature lower than or equal to that of the second temperature to allow formation of higher-order structures containing intercalators; (l) detecting the resulting higher-order structures; (m) performing melting temperature analysis; (n) detecting a waveform profile; and (o) determining a positive waveform profile from the sample if the sample contained the organism. In another embodiment, the third temperature is maintained for a second length of time about 40-60% (e.g., 50%) of the first length of time. In another embodiment, the number of times steps (d)-(g) are repeated in step (h) is 20-50 times (e.g., 22-24 times). In another embodiment, the method further comprises repeating steps (i)-(j) one or more times prior to step (k).

Thus, the invention provides a method of detecting the absence or presence of an organism in a sample, the method comprising, in this order, the steps of: (a) acquiring the sample; (b) isolating at least one copy of the genomic material of the organism, if present, in the sample; (c) aspirating at least one sample droplet into a microfluidic reaction channel; (d) forming at least one sample plug by mixing the at least one sample droplet with a primer plug, wherein the primer plug comprises, e.g., amplification reagents; (e) heating the at least one sample plug to a first temperature that will cause each copy of the genomic DNA, if present, to denature into a first and second genomic DNA template; (f) cooling the at least one sample plug to a second temperature to cause primers in the primer plug to anneal to each genomic DNA template; (g) reheating the at least one sample plug to a third temperature that is between the first and second temperatures as to allow the primers to remain annealed to the genomic DNA and the DNA polymerase to elongate nucleic acid polymers originating from the annealed primers; (h) maintaining the third temperature for a first length of time; (i) repeating steps (e)-(h) at least once; and (j) detecting any resulting amplified products, wherein at least steps (c)-(j) occur within an apparatus of the invention. In another embodiment the method further comprises, after step (i) and before step (j), the steps of (1) repeating steps (e)-(g); (2) maintaining the third temperature for a length of time equal to about 40-60% of the first length of time; and (3) cooling the at least one sample plug to a fourth temperature lower than or equal to that of the second temperature to allow formation of higher-order structures containing intercalators. In another embodiment of the invention, the detecting step of step (i) occurs at one temperature. In another embodiment of the invention, the detecting step of step (i) occurs at a range of temperatures. In another embodiment of the invention, the method further comprises a last step of selecting a DNA sample plug for further analysis, wherein the step of selecting occurs at a valve within an apparatus of the invention. One of skill in the art will recognize the detecting step in the embodiments described above will result in screening, quantification, identification, and/or optionally selection for further analysis of DNA that is present in the sample.

The invention thus provides a method of using an apparatus of the invention to screen a sample supply for contamination, comprising the steps of continuously aspirating sample droplets from the sample supply into at least one microfluidic inline reaction channel, forming sample plugs by mixing each sample droplet with a primer plug, amplifying DNA in sample plugs comprising genomic material, and detecting the absence or presence of amplified DNA products, wherein the steps occur in an apparatus of the invention. In this embodiment of the invention, the continued absence of amplified DNA products (i.e., zero-detection) is indicative of a clean sample supply. In contrast, the presence of amplified products is indicative of a contaminated sample supply.

The invention also provides a method of identifying an organism using an apparatus of the invention, the method comprising the steps of (a) preparing at least one DNA sample droplet comprising a DNA molecule isolated from the organism, (b) acquiring the at least one DNA sample droplet from the sample into at least one microfluidic reaction channel, (c) forming at least one DNA sample plug by mixing the at least one DNA sample droplet with a primer plug, wherein the primer plug comprises at least one known first primer, (d) subjecting the at least one DNA sample plug to at least one amplification cycle such that the at least one DNA sample plug has detectable amplified DNA products, (e) detecting amplified DNA products, (f) identifying the organism based on the detection of amplified DNA products, and (g) optionally repeating steps (a)-(f) with amplification reagents comprising a known primer that is different than the first known primer to increase the accuracy of the identification of the organism, wherein steps (b)-(e) occur within an apparatus of the invention. In one embodiment of the invention, the detection of amplified DNA products provides the identification of the organism from which the DNA was isolated because the primer was chosen to confirm the identity of an organism, e.g., a specific TAQMAN® primer that specifically binds to the genomic DNA of a particular organism may be chosen such that detection of amplified products using the method(s) described above confirms the identity of the organism. In another embodiment, waveform primers or SGP primers of the invention are used and the detected waveform profile provides the identity of the organism.

The invention also provides a method of quantifying the level of contamination in a sample supply, i.e., the concentration of genomic material in a sample. The quantification method of the invention using an apparatus of the invention comprises the steps of (a) diluting the sample using dilution factors such that the concentration of the genomic material is at most approximately one molecule per sample droplet, (b) acquiring sample droplets from the sample into at least one microfluidic inline reaction channel, (c) forming at least one sample plug by mixing each sample droplet with a primer plug, (d) subjecting each sample plug to amplification cycles such that each sample plug comprising a DNA molecule has detectable amplified DNA products, and each sample plug not comprising a DNA molecule will not have amplified DNA products, (e) detecting the absence or presence of amplified DNA products in each sample plug, (f) determining the ratio of sample plugs comprising amplified products to sample plugs resulting in zero-detection, and (g) using the dilution factor to calculate the original concentration of contaminating DNA in the sample, wherein at least steps (b)-(e) occur in an apparatus of the invention.

Sequencing analysis of genomic material is a definitive method of classifying an organism. As such, it is another object of the invention to provide a method of using an apparatus of the invention to allow for genomic material be further analyzed, e.g., such that detailed sequence information regarding genomic material that has been analyzed using any of the methods of the invention described above may be provided. Consequently, the invention provides a method in which a DNA sample plug that has traversed through a reagent assembly area, an amplification area, and/or a detection area of a microfluidic device of the invention may be optionally selected for further sequencing analysis. The selection process will occur at the "valve" of a microfluidic device of the invention. Upon selection, the valve of a microfluidic device of the invention will allow the selected DNA sample plug(s) to proceed to a device for sequencing, e.g., a DNA sequencing chip.

In another embodiment, the invention provides the methods of the invention further comprising a step wherein the sample plug(s) is surrounded by an immiscible nonaqueous fluid.

BRIEF DESCRIPTION OF THE DRAWINGS

FIG. 4: Nucleotide sequence of a theoretical genomic DNA.

FIG. 6: Sequences of each of the SGP nucleic acid polymers to be generated using the genomic DNA and primer of FIG. 5.

FIG. 7: Sequences of each of the SGP-SGP nucleic acid polymers to be generated after mPCR amplification of the SGP nucleic acid polymers of FIG. 6.

FIG. 8: Sequences of the SGP-SGP nucleic acid polymers (not underlined) and shortened SGP nucleic acid polymers (underlined) to be generated after the SGP-SGP nucleic acid polymers of FIG. 7 are subjected to a half-time elongation step.

DETAILED DESCRIPTION OF THE INVENTION

Figures 1A, 1B:
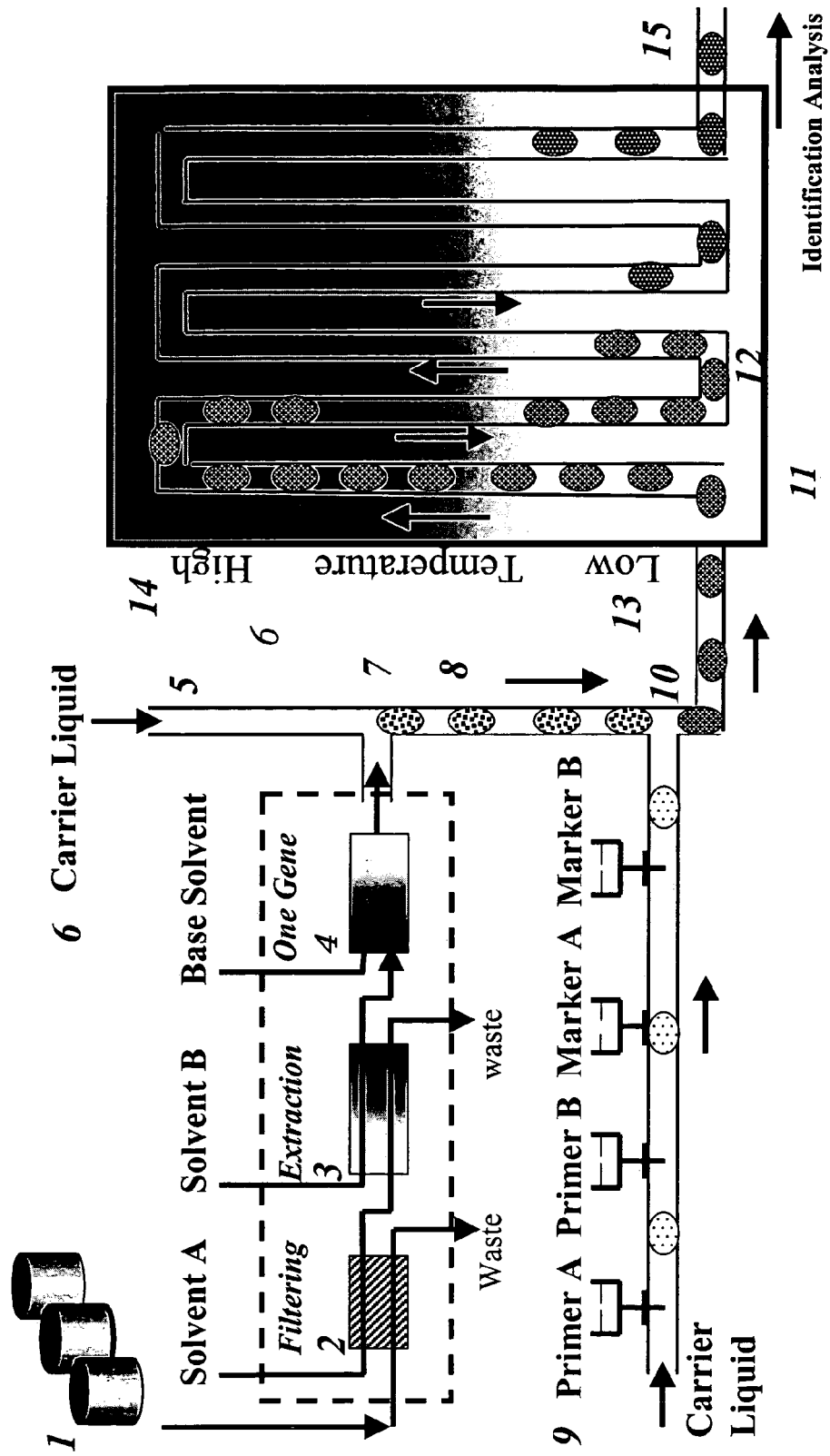
FIG. 1: Diagram delineating the path a sample droplet as it is (A) prepared (e.g., filtered, extracted, diluted, etc.), aspirated into a microfluidic inline reaction channel of a microfluidic device of the invention, mixed with amplification reagents to form a sample plug in the reagent assembly area of the device, and (B) is amplified within the amplification area of the microfluidic device, i.e., a first temperature-controlled area.

The present invention provides an apparatus comprising microfluidic devices and instruments that control the fluid movement within, heating and cooling of, and data acquisition from such devices. An apparatus of the invention may be used as an automated inline platform capable of preparing (e.g., isolating, processing, mixing with reaction reagents, etc.), amplifying (e.g., by either or both methods of PCR and waveform profiling), detecting (i.e., screening for, quantifying, identifying) and/or optionally selecting for further analysis (e.g., sequencing) genomic material from an organism for the purposes of detecting and/or classifying an organism(s) in a sample.

Additionally the invention provides improvements to a method of waveform profiling such that the apparatus of the invention and methods used therewith may be performed on a small starting amount of DNA. The improvements to the waveform profiling method include improved primers that effectuate a modified version of PCR, i.e., exponential amplification of DNA. The improvements to the waveform profiling method also include a half-time elongation step in the amplification procedure that allows for the production of a set of shortened single-stranded nucleic acid polymers derived from a subset of the nucleic acid polymers formed by the modified version of PCR (i.e., mPCR). Those skilled in the art will recognize that the improvements to the waveform profiling method allow for the detection and/or classification of an organism, even if the organism is present in a small number, e.g., the number of organisms present in a sample at the onset of contamination of a water supply. The present invention thus provides an improved waveform profiling method that will aid in providing quality assurance related to many sources (e.g., environmental and medical) that may become contaminated with organisms, including, but not limited to, air, dust, water, blood, tissues, plants, and foodstuffs.

Additionally, the present invention provides methods of using the disclosed apparatus to prepare (e.g., isolate, process, mix with reaction reagents, etc.), amplify (e.g., by PCR, waveform profiling, etc.), detect (e.g., screen for, identify, quantify), and/or optionally select for further analysis (e.g., sequence) the DNA of an organism. In one embodiment, the invention provides a method for high throughput automated inline waveform profiling, whereby methods of waveform profiling, e.g., the improved method disclosed herein, are performed with the automated inline waveform profiling platform as disclosed herein. One of skill in the art will recognize that the present invention includes amplification and detection of a single genome, or a small number of genomes.

I. Automated Inline Platform of the Invention

Over the last few years, automated inline PCR platforms as described above have been developed to be compatible with a variety of existing fluorescent "mix-and-read" biochemistries such as TAQMAN®, Molecular Beacons, Epoch Eclipse Probes, and Allele Specific Amplification. To date no known automated inline platform developed for use with PCR is also capable of being used with waveform profiling. Additionally, no known automated inline platform allows for the selection of previously analyzed genomic material for further analysis, e.g., sequence analysis of a DNA sample after amplification of the sample. The present invention provides such a platform. An automated inline platform of the invention, i.e., an apparatus comprising a microfluidic device capable of producing and detecting DNA products amplified by either or both PCR and waveform profiling methods and an instrument capable of controlling the fluid movement within, heating and cooling of, and data acquisition from such a device, is described below. In addition, the apparatus may further comprise a cartridge (or a similar device, or a device that accomplishes a similar function) that interfaces between the instrument and a microfluidic device of the invention; such cartridges are well known in the art.

A. Microfluidic Devices of the Invention

Figures 2A, 2B:
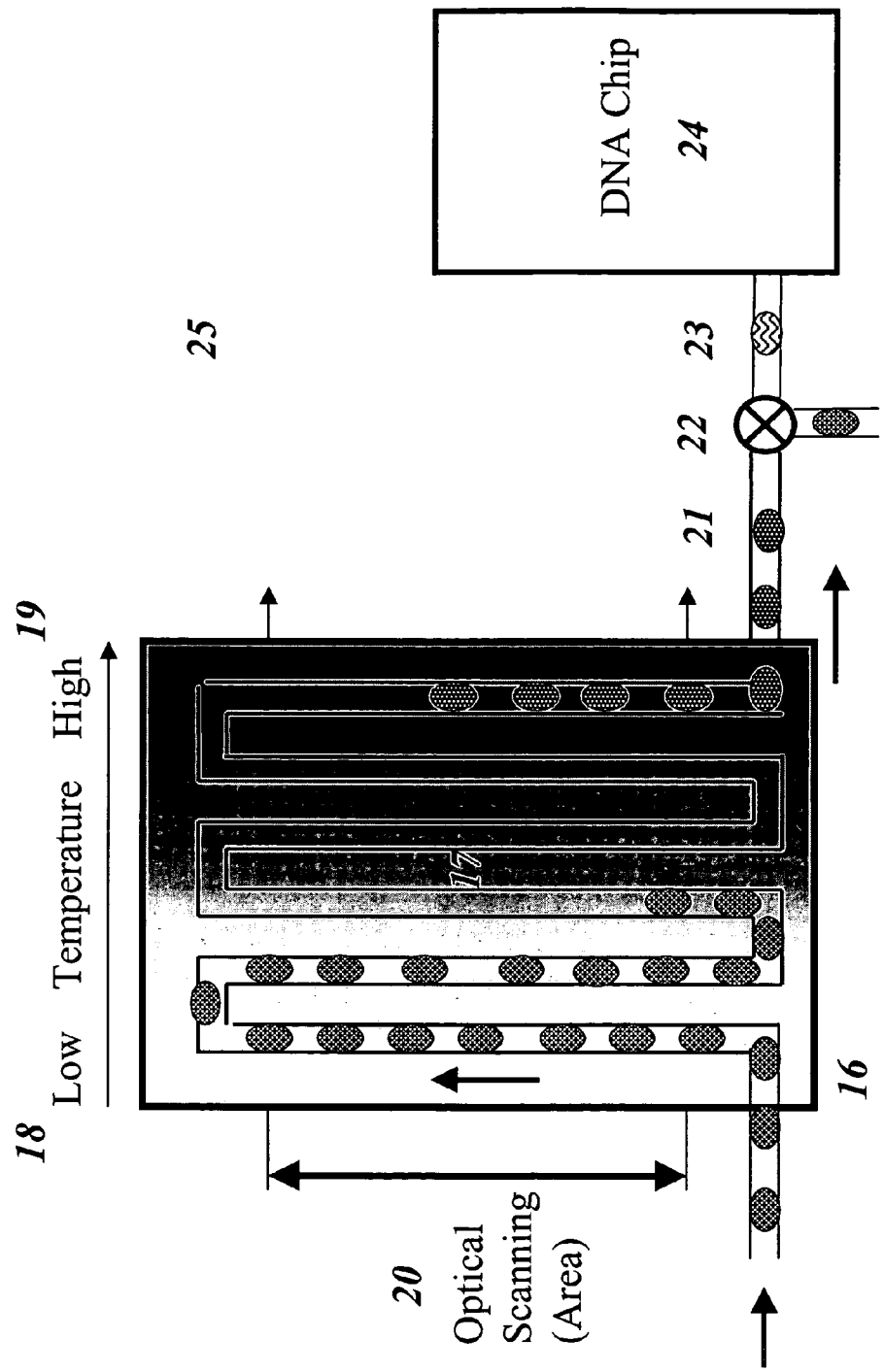
FIG. 2: Diagram delineating the path of a sample plug in a microfluidic inline reaction channel after it has passed a first temperature-controlled area of a microfluidic device of the invention (FIG. 1B) and is (A) passed through a detection area, i.e., the second temperature-controlled area, of a device of the invention and subjected to at least a first and second temperature and (B) selected as waste or for further analysis.

FIGS. 1 and 2 provide a schematic of a device of the invention and delineate the processes of sample plug preparation (FIG. 1A), amplification (FIG. 1B), detection (FIG. 2A) and selection (FIG. 2B), which may be commonly used for several different purposes, e.g., screening for, identifying, quantifying and/or further analyzing, e.g., sequencing, genomic DNA.

1. Preparing a Sample Plug

FIG. 1A delineates the process of preparing a sample plug. Briefly, a sample to be tested from sample containers (1) is sent to a filtering apparatus (2) for the collection of organic cells and the removal of sundries. Organic cells collected in sample liquid may be sent to an extractor apparatus (3) for the isolation of, e.g., viral, bacterial, etc., genomic material (e.g., removal of cell membranes, organelles, histones, debris, etc.). After isolation of the genomic material, the sample liquid and any isolated genomic material may be sent to a concentration adjuster (4) to adjust the concentration of the genomic material. The sample liquid from the concentration adjuster (4) is aspirated into a microfluidic inline reaction channel (5) and mixed with carrier liquid (6) at, e.g., a T-shaped junction (7) to form sample droplets (8) that may or may not comprise genomic material, e.g., at least one genomic DNA molecule.

As part of the sample plug preparation process, a primer apparatus (9) produces a series of primer plugs in carrier liquid comprising reagents required for DNA amplification and optionally detection. Each primer plug is combined with a sample droplet (8) at another junction, e.g., a T-shaped junction (10) to form a sample plug and complete the sample plug preparation process.

One of skill in the art will recognize that many types of samples may be tested using an automated inline platform of the invention. Such samples include, but are not limited to, water, air, dust, food, and biological samples, including body fluids (e.g., saliva, whole blood, plasma, urine, etc.), cells (e.g., whole cells, cell fractions, and cell extracts), and tissues. Biological samples also include sections of tissue such as biopsies and frozen sections taken for histological purposes. Preferred biological samples include blood, plasma, lymph, tissue biopsies, urine, CSF (cerebrospinal fluid), synovial fluid, and BAL (bronchoalveolar lavage).

The sample to be tested may be collected in a number of ways. For example, in the case of monitoring the purity of a water supply, a filtration system running parallel to the water supply can be checked at some determined interval (every hour, every 12 hours, etc.) by isolating any genomic material from a filter designed to capture bacteria, etc. Such a filtration system will concentrate the bacteria present in the water supply for more sensitive detection. Alternatively, samples may be taken directly from the water supply without filtration and/or concentration. Regarding other sources of samples, an air filtration system that captures, for example, bacteria may be employed; the material captured on such a filter would be placed in a solution to begin the isolation procedure. For other types of samples, additional steps will be necessary; for example, part of the initial procedure involved in using the present invention to detect bacteria in a blood sample would require separation of the bacteria from human blood components containing genomic material. Many techniques for isolating bacterial and/or viral genomic material from these exemplary samples and many others are well known in the art.

Isolation of any genomic material contained in a sample can be accomplished through a large number of techniques known to one of skill in the art. The isolation procedure should be a technique with a high capability for isolating and capturing genomic material, because in an embodiment of the invention, a sample plug comprising no genomic material is distinguished from a sample plug comprising as little as one genome. The full DNA genome from bacteria present in a water sample may be isolated using technologies well known in the art (e.g., one such set of technologies is available from Xtrana, Inc. (Broomfield, Colo.)).

Xtrana has developed different technologies for the following three sets of samples: (A) genomic DNA from whole blood, buffy coat, buccal swabs, and the bacteria *E. coli*; (B) RNA from tissue culture cells; and (C) genomic DNA from tissue culture cells, rodent tails, whole tissue, blood stains, and yeast. Briefly, the addition to the sample of plastic microbeads coated with XtraBind (Xtrana, Inc.), an electrophoretic, hydrophilic matrix, results in the adsorption of either RNA or DNA in a manner that is not sequence dependent and is essentially irreversible. One of skill in the art will recognize that since the methods herein describe DNA amplification processes, if the genomic material isolated is RNA, it must first be reverse transcribed into DNA, e.g., cDNA, prior to amplification. Methods of reverse transcription are well known in the art. In a preferred embodiment, the entire genomic DNA of an organism is isolated.

Other technologies available for the isolation of genomic DNA include technologies from Qiagen NA (Qiagen, Venlo, Netherlands); MagNAPure (Roche, Nutley, N.J.); KingFisher (Thermo Labsystems, Helsinki, Finland); and RevPrep Orbit (GeneMachines, San Carlos, Calif.).

Once the genomic DNA is isolated from a sample, its concentration within the sample liquid may be adjusted. In one embodiment of the invention, the concentration is adjusted such that a sample droplet comprises only one genomic DNA molecule (i.e., the genomic material from only one organism) or no genomic material. In another embodiment, the concentration may be about 0.5 DNA molecules per sample droplet. Alternatively, concentration may be expressed in terms of the percent probability that a sample droplet will comprise more than one DNA molecule. In another embodiment, the probability that a sample droplet will comprise two or more DNA molecules is, e.g., less than three percent.

Upon adjusting the concentration of genomic material from the sample, the sample liquid is repeatedly aspirated into a microfluidic inline reaction channel to form successive sample droplets of carrier liquid. Preferably, each sample droplet is approximately 1-2 nl, or, e.g., about 100 µm in length in a microfluidic inline reaction channel that is approximately 100 µm in diameter. These repetitive sample droplets may or may not comprise genomic material (e.g., genomic DNA); and may also be considered DNA sample droplets if they do comprise genomic material. Additionally, sample droplets may comprise any beads used in the isolation procedure, e.g., Xtrana beads. Alternatively, any beads used in the isolation procedure may be removed prior to aspiration of the sample droplet.

Generally, a microfluidic inline reaction channel may be 50 µm to 300 µm in diameter, and is typically 100 µm in diameter. A microfluidic inline reaction channel may be formed in glass, quartz or plastic. Methods of forming microfluidic inline reaction channels are well known in the art. Additionally, a skilled artisan will recognize that a microfluidic inline reaction channel may take many different paths, e.g., it may be straight, may form a joint or union with another microfluidic inline reaction channel at a confluent junction, may separate into two or more microfluidic inline reaction channels at a separate junction, may allow the fluid within it to pool and/or mix, etc., and may be formed with different materials depending on the area of the device, e.g., may be formed with transparent material when it is within the detection area of a microfluidic device.

Generally, carrier liquid (6) is a water-based liquid that is the same liquid as the sample liquid. Additionally, the carrier liquid may be an organic-based liquid, e.g., silicon oil of about 60 poise, or some other immiscible nonaqueous fluid. In one embodiment of the invention, repetitive sample droplets are aspirated into a microfluidic inline reaction channel and buffer spacers separate the sample droplets. In a preferred embodiment, an immiscible nonaqueous fluid (e.g., mineral oil) or some other hydrophobic substance is used as a buffer spacer, and is added to each, or between each, sample droplet being drawn by the sipper in order to surround and separate each sample droplet comprising DNA (or free of DNA) from the preceding or following sample droplet as they travel through a microfluidic inline reaction channel of the invention. Mineral oil is known to those of skill in the art as an appropriate substance for separating repetitive DNA samples. In addition, the inner wall of the microfluidic channels of a microfluidic device of the invention may be treated with an immiscible nonaqueous fluid (e.g., mineral oil) or some other hydrophobic material. This set of improvements with hydrophobicity will decrease or prevent cross-contamination between sample droplets. In other words, despite the movement inherent in microfluidics, the hydrophobic/hydrophilic difference between the carrier liquid and buffer spacer enables a single DNA molecule to be kept in the droplet (8) or plug during its movement along a microfluidic inline reaction channel without mixing with the buffer space, or with adjacent droplets or plugs.

In a microfluidic device of the invention, each sample droplet is further prepared at a junction, e.g., a T-shaped junction (10) to form a sample plug by being mixed with a primer plug comprising amplification reagents (e.g., primer(s), nucleotides, polymerase, etc.) and optionally detection reagents (e.g., detectable agents, e.g., labels, fluorescent probes, intercalators, etc.). A skilled artisan will recognize which amplification reagents should be mixed with each sample droplet and at what concentrations the reagents should be used. For example, amplification reagents typically include a polymerase, dNTPs, magnesium, buffer, and a primer or a pair of primers. One of skill in the art will also be able to determine the primer or primer pair to be used; e.g., if PCR is described, a skilled artisan will know to use a primer pair. In contrast, if the artisan wishes to perform waveform-profiling analysis, a waveform or SGP primer will be chosen. The design and selection of such primers are well known in the art. Additionally, detection reagents and methods of using such reagents to directly or indirectly label amplified DNA products are well known.

After a sample droplet has been aspirated into a microfluidic inline reaction channel, separated from other sample droplets to prevent cross-contamination, and mixed with amplification reagents to form a sample plug, it is drawn along the microfluidic inline reaction channel into an amplification area of a device of the invention, i.e., a first temperature-controlled area. A skilled artisan will recognize that similar to a sample droplet, a sample plug may or may not comprise genomic material, and may also be considered a DNA sample plug if it does comprise genomic material. Additionally, a skilled artisan will recognize that only DNA sample plugs will comprise DNA that will be amplified within a first temperature-controlled area of a device of the invention.

2. Amplifying DNA in DNA Sample Plugs

FIG. 1B provides a nonlimiting example of how a device of the invention may effectuate amplification of DNA that may be present in a sample plug after it has been prepared as described above. As sample plugs (which comprise sample droplets combined with primer plugs) are continuously drawn along an inline microfluidic reaction channel (5), they are introduced to an amplification area, i.e., a first temperature-controlled area, which may be, e.g., a thermal control plate (11). The path (12) of the microfluidic inline reaction channel may be such that it allows each sample plug to move in a winding and reciprocated way between low temperature areas (13) and high temperature areas (14) of the thermal control plate (11).

A skilled artisan will recognize that 1) the temperatures of the low temperature areas (13), the high temperature areas (14), and areas between the low and high temperature areas, 2) the path (12) of a microfluidic inline reaction channel, and 3) the speed with which a sample plug moves though a microfluidic inline reaction channel, may be appropriately adjusted according to the chosen amplification method. For example, the low temperature area (13) may be set to a temperature appropriate to effectuate annealing and the high temperature area (14) may be set to a temperature to effectuate denaturing. Additionally, the path (12) of a microfluidic inline reaction channel may be designed to allow a sample plug to move in a reciprocated way between the low temperature and high temperature areas to effectuate, e.g., approximately 20 to 40 cycles of denaturation, annealing, and elongation. Finally, the speed with which a sample plug (or DNA sample plug) flows through a microfluidic inline reaction channel may be set to allow each sample plug (or DNA sample plug) to remain at a denaturing, annealing, or elongating temperature for an appropriate length of time.

As previously described, each microfluidic inline reaction channel, or portions thereof, may also be rapidly heated and cooled in a localized and/or repeated manner such that the denaturing, annealing, and elongation steps of an amplification method (e.g., PCR, waveform profiling, SGP (described in detail herein)), are executed as a sample plug moves along a microfluidic inline reaction channel and through a first temperature-controlled area of a device of the invention. For example, Joule heating (see, e.g., U.S. Pat. Nos. 5,965,410 and 6,670,153) may be used to apply voltage to metal traces along side or crisscrossed with each microfluidic inline reaction channel of a device of the invention. Alternative methods of heating microfluidic inline reaction channels, e.g., use of hot water, air, etc., are well known in the art. Additionally, cooling of a microfluidic inline reaction channel, or portions thereof, may be achieved through the use of cooling fluid that travels through a coil to carry away thermal energy, or by allowing rapid heat dissipation. Similarly to methods of heating, alternative methods of cooling microfluidic inline reaction channels are well known.

One of skill in the art will recognize the temperatures, the length of time at such temperatures, and the number of cycles to which a DNA sample plug must be subject to effectuate amplification of DNA for the different methods of using an apparatus of the invention, e.g., screening, identification, quantification, etc. For example, in a preferred embodiment, denaturing temperatures are between 90° C. and 95° C., annealing temperatures are between 55° C. and 65° C., and elongation temperatures are dependent on the polymerase chosen (e.g., the optimal elongation temperature is about 72° C. for Taq polymerase). Also, a skilled artisan will recognize that that "hot starts" often begin PCR amplification methods, and that a final incubation of a DNA sample plug at 75° C. may optionally be added to the end of any amplification method.

A sample plug may be moved through a microfluidic inline reaction channel at different speeds ranging between 50 μm per second to 5000 μm per second, e.g., 500 μm per second. A skilled artisan will recognize that varying the speed with which a sample plug moves through a microfluidic inline reaction channel may effectuate the duration of time a sample plug remains at a certain temperature (e.g., temperatures required for denaturing, annealing, elongation, etc.). For example, although a typical cycling profile is ~94° for 1 min., 60° for 1 min., 72° for 1 min. (a typical rule for a 72° C. elongation is 1 minute for each 1000 base pairs being amplified), etc., a skilled artisan will recognize that the duration of time a sample plug remains at a certain temperature is dependent on the volume of the reaction, the concentration of the genomic DNA, etc., and consequently, the timing may differ from the typical cycling profile when using a microfluidic device of the invention. A skilled artisan will recognize that shorter durations at each temperature may be sufficient. Additionally, a skilled artisan will be able to determine the appropriate path required of a microfluidic inline reaction channel to effectuate the number of amplification cycles required.

After a sample droplet has been prepared, aspirated into a microfluidic inline reaction channel, separated from other sample plugs to prevent cross-contamination, mixed with amplification reagents to form sample plugs, and the DNA within DNA sample plugs amplified, each sample plug is driven along the microfluidic inline reaction channel into a detection area of the device, which may also be a second temperature-controlled area. A skilled artisan will recognize that only DNA sample plugs will comprise detectable amplified DNA products.

3. Detecting the Absence or Presence of Amplified DNA Products

A microfluidic device of the invention is designed to (1) allow DNA to be aspirated as a sample droplet(s) into a microfluidic inline reaction channel, (2) form sample plugs in a reagent assembly area by mixing sample droplets with primer plugs comprising amplification reaction components and/or detection components, (3) effectuate the amplification of DNA as a DNA sample plug is advanced along the microfluidic inline reaction channel through an amplification area, i.e., a first temperature-controlled area, and (4) allow for the detection of amplified DNA products as the DNA sample plug passes through the detection area. Additionally, a microfluidic device of the present invention is designed with at least one of two innovations.

One novel aspect of a microfluidic device of the invention comprises placing a microfluidic inline reaction channel passing through a detection area within a second temperature-controlled area. Placement of a microfluidic inline reaction channel passing through the detection area within a second temperature-controlled area will allow sample plugs traveling along the microfluidic inline reaction channel to be subject to a temperature sweep during detection. One of skill in the art will recognize that detecting sample plugs as they are subject to a temperature sweep, e.g., detecting the fluorescence of a DNA sample plug at different temperatures, allows for melting temperature analysis of, e.g., amplified DNA products. As such, the invention provides a microfluidic device, comprising at least one sipper; at least one fluid reservoir connected to at least one microfluidic inline reaction channel, wherein the at least one microfluidic inline reaction channel runs through a reagent assembly area, an amplification area within a first temperature-controlled area, and a detection area within a second temperature-controlled area; and at least one metal trace for heating of and/or fluid movement within the microfluidic inline reaction channel, wherein detection of amplified DNA products may occur at more than one temperature.

FIG. 2A provides an example of a detection area of a microfluidic device of the invention. As a sample plug with no amplified DNA or a sample plug with amplified DNA is drawn along a microfluidic inline reaction channel (5, as in FIG. 1), it is introduced into a detection area, i.e., a second temperature-controlled area, which may be, e.g., a second thermal control plate (16). A microfluidic inline reaction channel may have a detection path (17) that allows the detection of the absence or the presence of amplified DNA in sample plugs, as the sample plugs move between lower temperature areas (18) and higher temperature areas (19). As sample plugs traverse through an optical scanning area (20), any detectable reagent (e.g., fluorescent probes, intercalators, etc.) may be optically excited, e.g., with three-color laser beams, and any resulting emissions may be measured.

Generally, the lower temperature areas (18) of the detection area may be set to temperatures ranging between about 25° C. to about 65° C. The higher temperature areas (19) of the detection area may be set to temperatures ranging between about 55° C. to about 95° C. In the case that PCR amplified DNA is to be detected, the lower temperature areas (18) and higher temperature areas (19) of the detection area (16) may be set to one temperature, e.g., between about 25° C. to about 55° C.

The various instruments that may be used to regulate the temperatures in the detection area, excite detectable reagents in DNA sample plugs, and detect emissions, or a change in emissions, are well known in the art. For example, in one embodiment of the invention, the temperature may be measured with, e.g., an infrared charge-coupled device (CCD) (not shown) covering the optical scanning area (20), or a larger or smaller scanning area. In a preferred embodiment, placement of precise temperature sensors on the second thermal control plate to calibrate the infrared CCD is recommended to increase the accuracy of temperature measurements.

A skilled artisan will recognize that subjecting a sample plug (e.g., a DNA sample plug) to a temperature sweep in the detection area will enable detection of a waveform profile that results from a waveform profiling method, e.g., a method as described above, the SGP method as described herein, etc. In other words, as sample plugs traverse between temperatures, a correlation between any resulting emissions and the temperature of a sample plug may be determined. Additionally, PCR amplified DNA may also be detected as DNA sample plugs are subject to a temperature sweep, although the emissions need only be detected at one temperature. Alternatively, the lower temperature areas and higher temperature areas may be set to one temperature for the detection of PCR-amplified DNA.

As described above, an optical system in the detection stage (not shown in FIG. 2A) may be used to detect the change in emissions from amplified DNA, e.g., higher order structures, as the amplified DNA is subject to a temperature sweep. In other words, the optical system in the detection area may be used to measure, detect, and determine the waveform profile of isolated DNA. Detection of any waveform profile may indicate that the screened sample is contaminated, and subsequent comparison of the resulting waveform profile with a database of waveform profiles produced with a known primer and DNA isolated from a known organism may identify the contaminating organism. Additionally, if isolated genomic material was concentrated within the sample liquid, and the concentration known, the level of contamination may be quantified upon detection of the waveform profile.

A skilled artisan will recognize that use of a device of the invention for the preparation of genomic material, amplification of the isolated genomic material via a waveform profiling method, and detection of the resulting waveform profile is best utilized when little to no information is known regarding whether a sample is contaminated and/or what organism is contaminating a sample. One of skill in the art will also recognize that the identity of an organism (e.g., obtained from a waveform profile) may be further confirmed using a microfluidic device of the invention to isolate genomic material, amplify isolated genomic material via PCR, and detect the resulting PCR product(s). In one embodiment of the invention, the identification of the organism is further narrowed by forming several DNA sample droplets from the same organism, combining each DNA sample plug with a different primer chosen specifically to confirm the identity of an organism, amplifying each DNA sample droplet with a different primer (or set of primers) via PCR, and detecting the absence or presence of amplified products. Correlating the presence of amplified products with the particular primer(s) used may provide the identity of the organism.

As described above, screening for the presence of an organism, identifying the organism, and/or quantifying the concentration of the organism in a sample may be performed via waveform profiling and/or PCR using a microfluidic device of the invention comprising at least one sipper; at least one fluid reservoir connected to at least one microfluidic inline reaction channel, wherein the microfluidic inline reaction channel runs though a reagent assembly area, an amplification area within a first temperature-controlled area, and a detection area within a second temperature-controlled area; and at least one metal trace for heating of and/or fluid movement within the microfluidic inline reaction channel. When a more detailed examination of isolated genomic material is required, a microfluidic device of the invention may be used to select a DNA sample plug of interest for further analysis.

4. Selection of a DNA Sample Plug for Further Analysis

Although conventional DNA chips are used for many methods of DNA analysis, especially sequence analysis, because of their high flexibility and high performance, their high cost is a deterrent for their use in methods of screening and identifying a contaminating organism because there is a low probability of contamination in, e.g., a water supply, and consequently of isolating genomic material. Additionally, use of a DNA chip for quantification purposes is not cost-efficient because the accuracy of such quantification is not sufficient when there are multiple contaminating organisms or after exponential amplification with PCR. An apparatus of the invention solves these problems because it provides a cost-effective microfluidic device that may be used to screen a sample for contamination by an organism, to identify contaminating organisms (if any), and to quantify the level of contamination (for example, when using a microfluidic device of the invention, mere detection of amplified DNA in a DNA sample plug indicates the presence of a contaminating organism, analysis of the amplified DNA may provide the identification of the contaminating organism, and determining the ratio between the number of sample plugs with no amplified DNA to the number of DNA sample plugs with amplified DNA may provide the concentration of the contaminating organism within the sample, respectively). A skilled artisan will recognize that the accuracy of a device of the invention is several times that of a DNA chip, because a device of the invention uses a digital quantification method.

However, the sequencing capabilities of, e.g., DNA chips, may be more accurate than the sequencing capabilities that a microfluidic device of the invention may have, e.g., via detection of a waveform profile. Consequently, a microfluidic device of the invention may also be used to select a DNA sample plug of interest for further examination, e.g., sequencing analysis, e.g., using a DNA chip.

In one embodiment, a novel microfluidic device of the invention comprises a valve placed into a microfluidic inline reaction channel(s), wherein the valve is downstream of the detection area, such that if a DNA sample plug is selected for further analysis, e.g., sequencing analysis, the valve switches the flow within the microfluidic inline reaction channel and allows the DNA sample plug to flow away from, e.g., a waste well, and toward, e.g., a DNA sequencing chip. As such, the invention provides a microfluidic device comprising at least one sipper; at least at least one fluid reservoir connected to at least one microfluidic inline reaction channel, wherein the microfluidic inline reaction channel runs through a reagent assembly area, an amplification area, and a detection area, and wherein the microfluidic inline reaction channel further comprises a valve downstream of the detection area; and at least one metal trace for heating of and/or fluid movement within the microfluidic inline reaction channel.

FIG. 2B provides a nonlimiting schematic of how a sample plug (e.g., a DNA sample plug) is selected for further analysis. Sample plugs (21) move along a microfluidic inline reaction channel until they reach a selection valve (22) at a junction, e.g., a T-shaped junction. Based on data collected from the detection area of a microfluidic device of the invention (FIG. 2A), or based on other data, a DNA sample plug of interest (23) is selected for further analysis using, e.g., a DNA chip (24).

In one embodiment of the invention, a microfluidic device may have either or both 1) the detection area as a second temperature-controlled area, and 2) at least one microfluidic reaction inline reaction channel comprising a valve downstream of the detection area. As such, the invention also provides a microfluidic device comprising at least one sipper; at least one fluid reservoir connected to at least one microfluidic inline reaction channel, wherein the at least one microfluidic inline reaction channel runs through a reagent assembly area, an amplification area within a first temperature-controlled area, and a detection area of the body structure; and at least one metal trace for heating of and/or fluid movement within the microfluidic inline reaction channel, wherein detection of amplified DNA products may occur at more than one temperature, and wherein the at least one microfluidic inline reaction channel further comprises a valve downstream of the detection area of the body structure.

5. Manufacturing a Microfluidic Device of the Invention

The microfluidic devices of the invention may be manufactured by methods well known in the art; see, e.g., U.S. Pat. Nos. 6,500,323 and 5,882,465. Briefly, in designing the microfluidic devices of the invention, a driving force for moving the fluid sample plug(s) (e.g., a DNA sample plug(s)) through at least one microfluidic channel should be chosen, reaction parameters should be identified, and a channel network should be designed. Each of these steps is briefly outlined below.

As described in U.S. Pat. No. 6,500,323, a typical driving force for microfluidic systems, such as the automatic inline platform of the invention, is selected from pressure-based fluid transport systems, electrokinetic material transport systems, or hybrids of the two. Use of pressure-based systems is described in, e.g., U.S. Pat. No. 6,500,323; International Patent Application No. PCT/US98/20195; and U.S. patent application Ser. No. 09/245,627, filed Feb. 5, 1999, each of which is incorporated herein by reference. Use of electrokinetic forces to move fluids in a controlled fashion, and systems for carrying out such movement, are described in detail in, e.g., U.S. Pat. Nos. 5,800,690 and 5,779,868, each of which is incorporated herein by reference. An example of a hybrid system is described in, e.g., International Patent Application PCT/US98/20195. Although any one of the three systems may be used with the apparatus of the invention, it is preferred that the fluid be moved using a hybrid system.

As described in U.S. Pat. No. 6,500,323, reaction parameters, e.g., reaction reagents, reagent concentrations, reagent volumes, reaction times, and reaction temperature profiles, are important considerations to take into account when designing a microfluidic device of the invention. Since PCR and waveform profiling are well-known methods, their reaction parameters, e.g., reaction reagents, reagent concentrations, reaction times, temperature profiles, etc., are well established and, as such, easily accounted for in designing the channel networks of the microfluidic devices of the invention. For example, a microfluidic device designed for use with only PCR is detailed in U.S. Pat. No. 6,670,153, incorporated herein by reference. The design of the device described in U.S. Pat. No. 6,670,153 takes into consideration the reaction steps of PCR, i.e., denaturing, annealing, elongation, and "hot start." Because these steps are well defined for DNA amplification processes, including waveform profiling methods, e.g., the waveform profiling method described above, one of skill in the art will recognize that a microfluidic device of the invention may resemble that described in, e.g., U.S. Pat. No. 6,670,153, with the exception of one or both novel differences described above; i.e., placing any microfluidic reaction channel within the detection area within a second temperature-controlled area, thus allowing for detection of waveform profiles, and/or incorporating into at least one microfluidic reaction channel a valve that is downstream of the detection area, but upstream of the waste well. Additionally, one of skill in the art will be able to design a microfluidic device of the invention based on the reaction parameters of the SGP method described below.

As described above, the microfluidic devices of the invention may have at least one valve incorporated in at least one microfluidic channel, e.g., a valve placed downstream of the detection area and upstream of the waste well. Such valve may be visualized as a "T" intersection, cross intersection, "wagon wheel" intersections of multiple channels, or any other channel geometry where two or more channels, e.g., are in fluid communication. The chosen driving force, as described above, may controllably direct sample plug(s) (e.g., DNA sample plugs) through the valve by providing constraining flow from the other channels at the intersection. For example, in FIG. 2B, if a DNA sample plug (23) is selected for further analysis, it would be desirable for the DNA sample plug (23) to travel from left to right to, e.g., a DNA chip (24), and across and past the vertical channel leading to a waste well. As described in U.S. Pat. No. 5,876,675, incorporated herein by reference, an electrokinetic driving force may be used to direct the flow of the DNA sample plug by applying a voltage gradient across the length of the horizontal channel and pinching the material flow at the intersection. Additionally, when the valve is turned off, i.e., there is no voltage gradient across the length of the horizontal channel, the DNA sample plug travels from the left arm, through the intersection and into the bottom arm by, e.g., applying a voltage gradient across the vertical channel and/or applying a vacuum to the waste well located at the terminus of the horizontal channel.

B. Instrument for Controlling the Fluid Movement within, Heating and Cooling of, and Data Acquisition from a Microfluidic Device of the Invention Controlling devices (not shown in FIGS. 1 and 2) such as pumps, valves, sample plug (or DNA sample plug) position detectors, and a control computer may be used to control the movement and the timing of each sample plug and/or DNA sample plug to effectuate the above-mentioned processes. Such controlling devices are well known to those skilled in the art.

Instruments of the invention will include the capacity to establish, monitor, and control a second temperature-controlled area (for a temperature sweep) within the detection area of a microfluidic device of the invention. This will be accomplished by installing a temperature-controlled area, e.g., a fixed temperature gradient, similar to the heating region described in, e.g., U.S. Pat. No. 6,670,153, in the detection area of a microfluidic device of the invention, which enables the detection of amplified DNA products as they are subjected to a temperature gradient and enables the translation of such detection into a positive signal, a zero-detection, or a waveform profile. This modified system will be able to detect DNA products amplified by either or both PCR (e.g., TAQMAN®) and waveform profiling amplification methods. During TAQMAN® reactions, the temperature gradient in the detection area may be set to zero (so there will be a constant temperature in the detection area).

A skilled artisan will recognize well-known technology for controlling the fluid movement, heating and cooling of, and data acquisition from a microfluidic device of the invention, and thus, will be able to create such an instrument without undue experimentation.

II. Single Genome Profiling

Single Genome Profiling (SGP) permits analyzing and profiling genomic DNA from an organism, even if the organism is present in a small number, by providing improvements to waveform profiling methods. These improvements include novel primers, ("SGP primers") and a modified version of polymerase chain reaction (mPCR). SGP additionally provides a final "half-time elongation step." These improvements permit SGP (i.e., methods using SGP primers, mPCR, and a half-time elongation step) to result in the generation of distinct nucleic acid polymers ("SGP nucleic acid polymers"), each having a 5'-to-3' nucleotide sequence comprising the sequence of the SGP primer followed by a sequence complementary to one of several distinct regions of a genomic DNA template. In particular, SGP utilizes generated SGP nucleic acid polymers, the SGP primer, and mPCR to exponentially amplify "SGP-SGP nucleic acid polymers," each having a 5'-to-3' nucleotide sequence comprising the sequence of the SGP primer, a sequence identical to the sequence of one of several discrete regions of a genomic DNA template, followed by the reverse complement of the SGP primer. After exponential amplification of SGP-SGP nucleic acid polymers, SGP introduces a novel half-time elongation step to generate shortened versions of SGP nucleic acid polymers, i.e., "shortened SGP nucleic acid polymers," that will form higher-order structures. Since the genomic DNA of the organism is used as the initial template, SGP nucleic acid polymers and SGP-SGP nucleic acid polymers will contain sequences unique to the organism. For the same reason, and because the resulting SGP-SGP nucleic acid polymers are used for the generation of shortened SGP nucleic acid polymers during the half-time elongation step, single-stranded shortened SGP nucleic acid polymers will contain sequences unique to the organism. As such, in SGP, the single-stranded shortened nucleic acid polymers form higher-order structures based on the sequences unique to the organism. Accordingly, the set of higher-order structures formed by the single-stranded shortened nucleic acid polymers are unique to the organism. Consequently, detection of the different higher-order structures that are formed enables detecting and/or identifying the organism; such detection can be accomplished using, for example, fluorescent intercalators.

A. Modified PCR (mPCR) of Single Genome Profiling

One of skill in the art will recognize that many SGP nucleic acid polymers, and consequently, many SGP-SGP nucleic acid polymers and shortened SGP nucleic acid polymers may be generated using the modified PCR (mPCR) of the invention. Because each of these polymers originate from and contain an SGP primer at the 5'-end, one of skill in the art will recognize that many copies of the SGP primer must be added to a solution containing the genomic DNA of interest prior to the first cycles of mPCR in SGP. One of skill in the art will also recognize that the materials and conditions of mPCR are similar to those of PCR. For example, the appropriate concentrations of, e.g., dNTPs and reaction buffer, to add to PCR in addition to the primers and DNA templates are well known to a skilled artisan, as is the appropriate concentration of intercalators. The concentrations and amounts of SGP primer, nucleotides (i.e., dATP, dCTP, dTTP, and dGTP), DNA polymerase, reaction buffer, and/or magnesium that should be added prior to the first cycle of mPCR may be determined readily by a skilled artisan.

SGP is capable of analyzing the genomic DNA of organisms present in extraordinarily small amounts because it includes the step of mPCR. In one embodiment of the present invention, the genomic DNA of a single organism can provide the source template for a sufficient amount of shortened single-stranded nucleic acid polymers and associated higher-order structures for detection. This is because the mPCR step of SGP results in the exponential amplification of SGP-SGP nucleic acid polymers by virtue of the ability of the SGP primer to bind to and amplify certain SGP nucleic acid polymers in a manner somewhat similar to conventional PCR. However, there are two salient differences as compared with conventional PCR. First, the mPCR step utilizes only one primer, an SGP primer, which is capable of acting as both a forward and reverse primer. In contrast, conventional PCR uses two distinct primers: (1) a forward primer, and (2) a reverse primer that has a sequence different from that of the forward primer.

Second, whereas conventional PCR utilizes two primers to amplify a singular region of the genomic DNA, mPCR uses one primer to amplify several distinct regions of the genomic DNA, each of which are bracketed by a sequence identical to the SGP primer and a sequence complementary to the SGP primer, i.e., an "SGP primer binding site." The ability of mPCR in SGP to amplify several distinct regions of the genomic DNA is due to the use of one SGP primer that is capable of acting as a forward and a reverse primer. This characteristic of the SGP primer is a function of its length, which allows two key events to occur: (1) binding of SGP primers to several discrete SGP primer binding sites on each single-stranded genomic DNA template, and (2) binding of SGP primers to the SGP nucleic acid polymers (generated by at least one cycle of mPCR) that have a 5'-to-3' nucleotide sequence comprising the SGP primer sequence and the reverse complement of the SGP primer within its distinct nucleotide sequence. The presence of the reverse complement sequence within an SGP nucleic acid polymer and the subsequent binding of the SGP primer permits a PCR-like (i.e., mPCR) exponential amplification of several distinct double-stranded SGP-SGP nucleic acid polymers, i.e., the exponential amplification of several distinct regions of double-stranded genomic DNA that are bracketed by SGP primer binding sites.

SGP primers share some similar features with waveform primers, the latter described in detail in, e.g., Japanese Patent Application Publication Nos. 2003-334082 and 2003-180351. SGP primers are essential to SGP, and are characterized by their length. The length of an SGP primer is critical because the reduced length of the primer allows the primer to specifically bind to several discrete sites along the length of each single-stranded genomic DNA template, and because the reduced length also allows for the increased probability that SGP nucleic acid polymers will have a 5'-to-3' sequence comprising the reverse complement of the SGP primer sequence within its distinct nucleotide sequence.

The special characteristics of the SGP primer allow it to be used in the SGP method to result in the exponential, i.e., nonlinear, amplification of SGP-SGP nucleic acid polymers from certain SGP nucleic acid polymers during each cycle of mPCR after the first cycle. The first cycle of mPCR in SGP consists of the following steps: 1) denaturing each copy of the genomic DNA into two single-stranded genomic DNA templates, 2) annealing the SGP primer to several discrete SGP primer binding sites on each single-stranded genomic DNA template, and 3) elongating SGP nucleic acid polymers from each of several SGP primers bound to discrete SGP primer binding sites on each single-stranded genomic DNA template, wherein each SGP nucleic acid polymer has a 5'-to-3' nucleotide sequence comprising the bound SGP primer from which the SGP nucleic acid polymer is elongated, followed by a distinct nucleotide sequence that is complementary to the sequence of the genomic DNA template downstream of the bound SGP primer.

One of skill in the art will recognize that the "full-time" duration of the elongation step determines the length of the SGP nucleic acid polymers, and thus, SGP nucleic acid polymers created in one cycle may have distinct nucleotide sequences, but may be approximately the same length. For example, assuming the SGP primer is designed such that it will anneal to $10^3$ sites along each single-stranded genomic DNA template, and assuming that the timing of the elongation step is adjusted to produce SGP nucleic acid polymers of approximately 1 kb in length, one cycle of SGP amplification would result in $10^3$ distinct SGP nucleic acid polymers per template, each of which would be approximately 1 kb in length. Of course, if one of the SGP primer binding sites to which the primer annealed is less than 1 kb from the 3' end of a genomic DNA template, the elongation from the SGP primer bound at that site would produce an SGP nucleic acid polymer of less than 1 kb. In addition, if an SGP primer binding site (e.g., site "B") is within 1 kb downstream of another SGP primer binding site (e.g., site "A"), an SGP nucleic acid polymer of less than 1 kb will be generated from the SGP primer that bound at site A.

In SGP, a cycle of mPCR may be repeated several times, e.g., 15-100 times. One of skill in the art will recognize that during the denaturing step of each cycle, SGP nucleic acid polymers will become single-stranded, i.e., the SGP nucleic acid polymers will no longer be bound to a genomic DNA template. It is critical in SGP, during the annealing step in subsequent cycles of mPCR, that certain SGP nucleic acid polymers having a 5'-to'3' nucleotide sequence comprising the reverse complement of the SGP primer within their distinct nucleotide sequence remain accessible to binding by the SGP primer, i.e., that these certain SGP nucleic acid polymers do not form higher-order structures. It is well understood that the binding of SGP nucleic acid polymers either as part of a higher-order structure or to an SGP primer is dependent on several factors, e.g., the annealing temperature, the lengths of the SGP nucleic acid polymers and SGP primers, and the concentrations of the SGP nucleic acid polymers and SGP primers in the reaction mixture. Consequently, one of skill in the art will recognize that manipulating the annealing step of mPCR, e.g., by increasing the concentration of the SGP primer, may aid in preventing the formation of higher-order structures comprising SGP nucleic acid polymers. However, while adjusting these well-known factors may aid in practicing the invention, such adjustments are not absolutely required because the factor of SGP nucleic acid polymer stability is addressed in the design of the SGP primer. As noted below, the SGP primer is designed without a nonspecific stabilizing portion, and thus, SGP nucleic acid polymers, each having the sequence of the SGP primer at its 5'-end, will not be stable, i.e., will tend to bind to primer readily. Consequently, certain SGP nucleic acid polymers that have a 5'-to-3' sequence comprising the SGP primer sequence followed by the reverse complement of the SGP primer sequence within their distinct nucleotide sequence will bind selectively to SGP primers prior to formation of any higher-order structure.

The binding of SGP primers to the certain SGP nucleic acid polymers that have a 5'-to-3' sequence comprising the SGP primer sequence followed by the reverse complement of the SGP primer sequence within their distinct nucleotide sequence is what effectuates SGP mPCR amplification cycles subsequent to the first cycle. An SGP primer binding to its complement on SGP nucleic acid polymers promotes a PCR-like reaction that results in SGP-SGP nucleic acid polymers, each of which has a nucleotide sequence comprising a sequence identical to the sequence of one of the several discrete regions of a genomic DNA template that are flanked at the 5' end by a 5'-to-3' sequence identical to the SGP primer and at the 3' end by a 5'-to-3' sequence that is the reverse complement of the SGP primer. Accordingly, since each SGP-SGP nucleic acid polymer has at its 3' end a 5'-to-3' sequence that is complementary to the SGP primer, each SGP-SGP nucleic acid polymer will also be bound by the SGP primer prior to the formation of a higher-order structure in annealing steps of subsequent mPCR cycles. Consequently, subsequent cycles of mPCR will involve the exponential amplification of SGP-SGP nucleic acid polymers.

One of skill in the art will recognize that, although all SGP nucleic acid polymers will comprise the SGP primer sequence at the 5' end, only a certain percentage of the SGP nucleic acid polymers will also comprise the reverse complement of the SGP primer sequence within its 5'-to-3' distinct nucleotide sequence. The percentage of certain SGP nucleic acid polymers that participate in SGP-SGP nucleic acid amplification is dependent on several easily determined factors, such as the "full-time" length used for the "full-time elongation step" of mPCR, and the design of the SGP primer. For example, a potential SGP nucleic acid polymer may have the reverse complement of the SGP primer sequence approximately 750 bases (0.75 kb) downstream from the 5' end. In this example, assuming, as above, that the full-time elongation step of mPCR is set to produce 1 kb SGP nucleic acid polymers, the subsequent mPCR cycles will begin an mPCR exponential amplification of that 750-base (0.75-kb) region, i.e., double-stranded SGP-SGP nucleic acid polymers that have the same sequence of the region of double-stranded genomic DNA from which the original 1 kb SGP nucleic acid polymer was derived. This exponential amplification will also occur for any other single-stranded SGP nucleic acid polymer that has a 5'-to-3' sequence containing the reverse complement of the SGP primer within 1 kb downstream of its 5' end. Consequently, increasing the full-length elongation time will increase the probability that a higher percentage of SGP nucleic acid polymers will comprise one or more SGP primer binding sites within its nucleotide sequence. The converse is also true; decreasing the full-length elongation time will decrease the probability that a higher percentage of SGP nucleic acid polymers will comprise one or more SGP primer binding sites within its sequence.

The percentage of certain SGP nucleic acid polymers that comprise SGP primer binding sites within their sequence may also be manipulated by designing the primer, a fuller description of which is provided below, such that, e.g., 1 in 100 (i.e., $10^{-2}$) SGP nucleic acid polymers would contain an SGP primer-binding site within its sequence. In such an example, and assuming as above, that the SGP primer may anneal to $10^3$ sites along each single-stranded genomic DNA template, $2 \times 10^3$ different SGP nucleic acid polymers would be generated for each organism (i.e., $1 \times 10^3$ SGP nucleic acid polymers per template$\times$2 templates per organism), and approximately 20 distinct SGP-SGP nucleic acid polymers would be amplified. Of course, the location of the reverse complement relative to the site at which the primer initially binds will determine the length of each SGP-SGP nucleic acid polymer being exponentially amplified. Additionally, as with any PCR procedure, exponential amplification of the SGP-SGP nucleic acids of the invention occurs through mPCR cycles that involve elongation (resulting in double-stranded SGP-SGP nucleic acid polymers), denaturing (resulting in single-stranded SGP-SGP nucleic acid polymers available for annealing to SGP primers), and annealing of SGP primers (setting up the next cycle of elongation and amplification).

Thus, in mPCR, the multiple copies of one SGP primer added at the beginning of the first cycle will serve the function of the pair of primers usually utilized to accomplish PCR. In other words, a single SGP primer of the present invention will bracket several discrete regions of double-stranded genomic DNA and result in mPCR exponential amplification of those regions in the form of several distinct double-stranded SGP-SGP nucleic acid polymers.

B. Half-Time Elongation Step

As noted above, the waveform analysis that serves as the final goal of a waveform profiling method in SGP requires the presence of several distinct single-stranded nucleic acid polymers that represent the uniqueness of the genome; these nucleic acid polymers are combined with intercalators to form higher-order structures that are ultimately detected, and thus, necessary in this waveform profiling method.

In SGP, detectable higher-order structures commonly are not formed until after 1) the exponential amplification of SGP-SGP nucleic acid polymers has been accomplished through several cycles of mPCR using full-time elongation steps, and 2) the generation of single-stranded shortened SGP nucleic acid polymers from SGP-SGP nucleic acid polymers through the introduction of a half-time elongation step. Thus, the present invention introduces a "half-time" cycle of amplification into the mPCR procedure (after sufficient mPCR cycles have produced sufficient copies of the exponentially amplified polymers; e.g., $10^6$ to $10^7$ copies) in order to produce several copies of each shortened SGP nucleic acid polymer. In other words, by decreasing the amount of time, e.g., by 40-60%, of the elongation step for this mPCR cycle, a subset of the nucleic acid polymers derived from a subset of the SGP-SGP nucleic acid polymers are decreased in length, i.e., shortened SGP nucleic acid polymers. Because the shortened SGP nucleic acid polymers will no longer contain the reverse complement of the primer sequence on the 3' end of the polymer, shortened SGP nucleic acid polymers may not be exponentially amplified; i.e., they will remain single-stranded and will consequently form higher-order structures that may be detected.

It should be noted that SGP nucleic acid polymers (i.e., not shortened SGP nucleic acid polymers) not comprising a 5'-to-3' sequence identical to the reverse complement of the SGP primer would not be bound to primers during any cycle of mPCR amplification, and thus, may also form higher-order structures. However, as explained below, one half-time elongation step produces several copies of each distinct shortened SGP nucleic acid polymer (because they are derived from exponentially amplified SGP-SGP nucleic acid polymers). In contrast, SGP nucleic acid polymers not having a sequence comprising an SGP primer-binding site are only linearly amplified from a relatively small starting amount of genomic DNA. Consequently, the contribution of such SGP nucleic acid polymers to the formation of higher-order structures is negligible compared to the contribution of the shortened SGP nucleic acid polymers to the higher-order structures.

The higher-order structures produced in SGP will contain mostly shortened SGP nucleic acid polymers that are generated by introduction of the half-time elongation step. By way of example, assuming, as above, that the SGP primer could anneal to, e.g., approximately $10^3$ sites on each single-stranded genomic DNA template, the total number of SGP nucleic acid polymers from the first cycle may be, for example, approximately $2 \times 10^3$ SGP nucleic acid polymers per copy of genomic DNA (i.e., per organism). Also assuming, again as above, that the primer was designed such that 1 in 100 SGP nucleic acid polymers has a sequence comprising an SGP primer binding site within its sequence, approximately 20 SGP-SGP nucleic acid polymers, each of which is identical to one of several distinct regions of a genomic DNA template that are bracketed by SGP primer binding sites, will be exponentially amplified by mPCR, resulting in a relatively large number of copies of SGP-SGP nucleic acid polymers (approximately $10^6$-$10^7$ copies after 22-24 mPCR cycles when starting with a single genomic DNA). The number of exponentially amplified SGP-SGP nucleic acid polymers, and consequently the number of shortened SGP nucleic acid polymers derived therefrom, will dwarf the number of SGP nucleic acid polymers that continue to be produced by linear amplification as the cycles of amplification proceed.

One of skill in the art will recognize that the potential total number of SGP-SGP nucleic acid polymers produced by SGP is related to the size of the genome and the primer length. Thus the preferred number of SGP nucleic acid polymers produced in the first cycle of amplification may be determined as a function of the desired number of SGP-SGP nucleic acid polymers capable of producing shortened SGP nucleic acid polymers during the half-time elongation step (i.e., the desired number of shortened SGP nucleic acid polymers available for formation of higher-order structures). Such determination will be helpful in designing SGP primers of the invention, described in further detail below.

In determining the desired number of shortened SGP nucleic acid polymers available for the formation of higher-order structures, one of skill in the art will recognize that only a subset of the SGP-SGP nucleic acid polymers exponentially amplified by mPCR is used in the generation of shortened SGP nucleic acid polymers; such subset comprises the longer SGP-SGP nucleic acid polymers that are not able to fully elongate in a half-time elongation step. Since the sequences of SGP-SGP nucleic acid polymers being exponentially amplified by mPCR comprise the nucleotide sequence of the reverse complement of the primer at the 3'-end, a full-time elongation step is necessary to complete the elongation for this subset of SGP-SGP nucleic acid polymers, and the half-time elongation step will result in shortened SGP nucleic acid polymers, i.e., nucleic acid polymers that do not contain the reverse complement of the primer at the 3'-end. On the other hand, some of the SGP-SGP nucleic acid polymers being exponentially amplified by mPCR are considerably shorter than these longer SGP-SGP nucleic acid polymers. Such SGP-SGP nucleic acid polymers, which fully elongate in the time allotted in the half-time elongation step, will continue to be amplified exponentially in any subsequent cycles of mPCR; as described below, these SGP-SGP nucleic acid polymers commonly will not become part of the higher-order structures. One of skill in the art will recognize that, given the random location of the reverse complement of the SGP primer within the length of the SGP-SGP nucleic acid polymers that undergo exponential amplification with mPCR, the introduction of a half-time elongation step will result in approximately half of the SGP-SGP nucleic acid polymers being used to create shortened SGP nucleic acid polymers.

Approximately 50% of the exponentially amplified SGP-SGP nucleic acid polymers will not contain an SGP primer binding site within the portion elongated by the half-time elongation step, and thus will participate in the generation of shortened SGP nucleic acid polymers. Since the shortened SGP nucleic acid polymers will not comprise a sequence capable of binding to the SGP primer, they will form higher-order structures.

The other approximately 50% of the SGP-SGP nucleic acid polymers exponentially amplified by mPCR will still contain an SGP primer-binding site. Additionally, since the annealing of SGP-SGP polymers with complementary sequences to create double-stranded SGP-SGP polymers is stable and tends to occur quickly, SGP-SGP nucleic acid polymers commonly will not be utilized in the formation of higher-order structures.

For example, assuming that an SGP primer of 9 bases in length may anneal to 7,000 sites, and the resulting SGP nucleic acid polymers may be elongated to 2,000 bases in length, $1.4 \times 10^7$ bases of genomic DNA, i.e., 1/142 of a single-stranded genomic DNA template of, e.g., $2 \times 10^9$ bases in length, will be copied as SGP nucleic acid polymers. In SGP, approximately 50 to 70 of these 7,000 SGP nucleic acid polymers will comprise an SGP primer-binding site (assuming again, as above, that the SGP primer was designed such that approximately 1 in 100 SGP nucleic acid polymers will contain an SGP primer binding site). These approximately 50 to 70 SGP nucleic acid polymers will effectively generate SGP-SGP nucleic acid polymers that will be exponentially amplified during the mPCR step of SGP. After 22-24 cycles of mPCR and after the half-time elongation step, several copies (e.g., $10^6$ to $10^7$) of approximately 25-35 distinct shortened SGP nucleic acid polymers (which will form the higher-order structures) are expected to result from the exponentially amplified SGP-SGP nucleic acid polymers. Thus, the half-time elongation step not only produces shortened SGP nucleic acid polymers for the formation of higher-order structure, but also distinguishes among SGP-SGP nucleic acid polymers of different lengths.

As a further example, assume that among the several SGP-SGP polymers being amplified exponentially during the full-time mPCR cycles in SGP are SGP-SGP nucleic acid polymers of 1 kb, 0.8 kb, 0.6 kb, 0.4 kb, and 0.2 kb; also assume that the timing of the elongation step in these repetitive mPCR cycles is just sufficient for elongating a 1 kb polymer. One of skill in the art will realize that during the subsequent "half-time" elongation step, the resulting polymers produced will be approximately 0.5 kb, 0.5 kb, 0.5 kb, 0.4 kb and 0.2 kb, respectively. As this mPCR cycle progresses, and the newly elongated polymers of DNA are denatured from their individual complementary template strands, the first three listed polymers (i.e., the polymers of 0.5 kb in length, those copied from individual template strands that were originally of greater lengths (1 kb, 0.8 kb, and 0.6 kb)) will not have the reverse complement of the primer sequence at their 3' end, and they will all be of approximately the same length (i.e., 0.5 kb). These single-stranded shortened SGP nucleic acid polymers will be available to form the higher-order structures necessary for the generation of waveform profiles. However, the polymers elongated from individual template strands of 0.4 kb and 0.2 kb lengths will be full length, i.e., the reverse complement of the primer sequence will be present at the 3' end of these copies, and subsequent cycles of PCR amplification will continue to produce SGP-SGP nucleic acid polymers such that they will not be available to participate in the formation of higher-order structures.

C. Detecting the Single Genome Profile

Because exponential amplification, i.e., mPCR, is used in the SGP method, there is no requirement to begin with a large number of copies of the genomic DNA of interest. For example, assume that a (non-SGP) waveform primer may bind to $10^3$ sites along each single-stranded genomic DNA template and (because other waveform profiling methods generally require beginning the procedure with at least $10^6$ organisms, as described above) the total number of nucleic acid polymers produced per cycle of linear amplification is approximately $2 \times 10^9$ ($10^3$ nucleic acid polymers per genomic DNA template×2 genomic DNA templates per organism×$10^6$ organisms). In other waveform profiling methods, the linear amplification cycles would be repeated, e.g., 22-24 times (i.e., producing 22-24 sets of $2 \times 10^3$ different single strands). In contrast, one of the embodiments of the present invention is related to the fact that waveform profiling with the SGP method potentially can be accomplished if only a single copy of the genomic sequence is present in the sample at the beginning of the amplification process (assuming efficient extraction). After several cycles of mPCR amplification (e.g., 22-24 cycles), beginning with one copy of the genome, each distinct region of genomic DNA bracketed by SGP primer binding sites, i.e., each distinct SGP-SGP nucleic acid, will be copied on the order of $10^6$ to $10^7$ times (i.e., approximately $10^6$ to $10^7$ copies will be present). This improvement over other waveform profiling methods allows for far greater sensitivity in detecting and identifying, for example, the presence of bacteria in a sample using the SGP method.

Because the shortened SGP nucleic acid polymers elongated as described are derived from SGP-SGP nucleic acid polymers that are identical to regions of the genomic DNA bracketed by SGP primer binding sites, the shortened SGP nucleic acid polymers will comprise the unique sequence differences of the organism being detected. In SGP, the copies of each of the several single-stranded shortened SGP nucleic acid polymers produced during the half-time elongation step will interact with each other to form higher-order structures, i.e., complexes comprising a number of shortened SGP nucleic acid polymers. The higher-order structures will have different stabilities and dissociate at different melting temperatures (Tm) depending on the base sequences of the shortened single-strands, i.e., based on the unique genomic information of the organism. The Tm of the higher-order structures derived from an organism can be determined and recorded; this is accomplished with the use of fluorescent agents that intercalate into higher-order DNA structures, i.e., intercalators. Thus, SGP may be used to detect, compare and distinguish the genomic DNAs of different organisms through waveform profile analysis, i.e., detecting and recording the dissociation of higher-order structures.

The higher-order structures of a particular sample are dissociated by increasing the temperature of the sample. As the higher-order DNA structures dissociate, the fluorescent agents intercalated in these higher-order structures also dissociate. Plotting the rate of change of fluorescence intensity obtained by the dissociation of these higher-order structures as a function of increasing temperature produces a waveform that is unique to the genomic DNA of the organism, i.e., higher-order DNA structures at different melting temperatures (Tm) are observed and recorded to produce a characteristic waveform profile. A waveform profile that indicates the presence of an organism in the sample is termed a positive waveform profile; in the event that no organism is present in the sample, a negative waveform profile is produced.

In some embodiments of the present invention, the presence of an appropriate (positive) waveform profile is indicative of the presence of an organism in a sample. In other embodiments, a characteristic waveform profile is indicative of a particular species (or strain) of an organism, e.g., a species or strain of bacteria. Thus, the SGP method can distinguish between the genomic DNA from a first organism and the genomic DNA from a second organism using intercalators to obtain a unique waveform profile for each organism using a method of waveform profiling.

As described above, the mPCR step of SGP comprises multiple cycles of amplification; i.e., multiple cycles of the following steps: 1) denaturing each genomic DNA into genomic DNA templates, 2) annealing SGP primers to several discrete SGP primer binding sites along each genomic DNA template and any previously generated SGP nucleic acid polymers and SGP-SGP nucleic acid polymers, and 3) elongating SGP and SGP-SGP nucleic acid polymers from each primer that annealed to an SGP primer binding site. In particular, during one cycle of amplification, the temperature of the sample is increased (e.g., to 95-98° C.) to denature any double-stranded nucleic acid polymers (including genomic DNA). The temperature is subsequently decreased (e.g., to 25° C.) to allow SGP primers to anneal to any available SGP primer-binding site. The final step in the cycle, elongation of SGP and SGP-SGP nucleic acid polymers from the primer, is performed at ~72° C. using, e.g., Taq polymerase. Finally, in one of the last cycles of amplification, the length of time for the elongation step is reduced, e.g., by 40-60% (e.g., by 50%), to generate shortened SGP nucleic acid polymers. One of ordinary skill in the art will appreciate that additional cycles incorporating additional half-time elongation steps may be included in the present invention to produce a more accurate and/or robust waveform profile, and that these cycles may follow additional cycles incorporating additional full-time elongation steps included to amplify the products (e.g., SGP-SGP nucleic acid polymers of the invention).

One of skill in the art would know to employ an apparatus or machine capable of the repetitive cycling steps involving the alterations in temperature necessary for the denaturing, annealing, and elongation steps inherent in amplification procedures; such machines include, but are not limited to the apparatus of the invention, PCR machines known in the art, and the "Genopattern Analyzer GP1000" machine (Adgene). Other companies that produce devices capable of the mPCR cycling steps necessary in the present invention include, but are not limited to, Perkin-Elmer (Wellesley, Mass.), Applied Biosystems (Foster City, Calif.), or MJ Research (Waltham, Mass.). Such machines are capable of altering the timing and duration of various steps in which temperatures are changed and reset, and thus such machines would be useful in producing both the full-time elongation steps and the essential half-time elongation step of the present invention. In addition, one of skill might employ additional materials to assist in the various aspects of using SGP to detect the genomic DNA of organisms, including but not limited to reagent kits for extraction (of which there are several known in the art; e.g., Xtrana technologies, such as the XTRA AMP® extraction system (Xtrana Inc., Broomfield, Colo.)); analytical software to interpret the results produced by waveform profiling (e.g., GenoMaster by Adgene); and primer-design supporting tools (such as the "Design Support Tool for Genopattern Primer" used in other waveform profiling methods, and GenoSequenceAnalyzer software, both by Adgene). One of skill in the art would adjust the parameters and/or protocols of such software and/or tools to be useful for SGP.

D. Single Genome Profiling Primers

An SGP primer is designed, using methods well known in the art, such that it binds to several discrete sites along each single-stranded genomic DNA template. In one embodiment of the invention, SGP primers are used to detect the presence of any genomic DNA from an organism, e.g., bacteria and viruses. In another embodiment of the invention, SGP primers are tailored for use in detecting particular organisms, e.g., a particular species or strain of bacteria. One of skill in the art can determine the length and sequence of an SGP primer that is used to detect the genomic DNA of bacteria generally, or of a particular species or strain of bacteria, by taking into account the length and sequence of the genomic DNA. One of skill in the art would survey several species of bacteria regarding the sequences of their genomic DNAs and deduce the sequence of a primer capable of detecting most or all of these species; this type of primer is sometimes referred to as a "universal" primer. Universal SGP primers, and SGP primers specific for a particular species or strain, are determined after straightforward experimental trials conducted by one of ordinary skill in the art.

One of skill in the art will appreciate that the length of the SGP primer and its ability to bind to several SGP primer binding sites, i.e., complementary sequences, along genomic DNA templates are inversely related, i.e., the shorter the length of the primer, the greater the number of discrete SGP binding sites along a genomic DNA template to which the primer will bind. Conversely, the longer the length of the primer, the fewer the number of discrete SGP primer binding sites along a genomic DNA template to which the primer will bind. In addition, the same analysis related to primer length applies to the probability that the complementary sequence of the SGP primer and the reverse complementary sequence of the SGP primer will occur within a preset distance along the length of a genomic DNA template (i.e., the preset maximum length of an SGP nucleic acid polymer). Thus the shorter the length of the primer, the greater the likelihood that the reverse complement of the SGP primer binding site will be present within a preset distance downstream from the SGP primer binding site. One of skill in the art will recognize that the preset distance will be determined by the length of time comprising the full-time elongation step, and when the reverse complement of the primer binding site is present within that preset distance, exponential amplification will occur. Finally, one of skill in the art will also recognize that the sequence content plays a role in the design of a primer. Designing primers generally with these factors in mind has become a routine method in the art (see generally, e.g., Burpo (2001) "A critical review of PCR primer design algorithms and cross-hybridization case study," available in "Computational Molecular Biology" course materials, Stanford University (cmgm.stanford.edu/biochem218/Projects%202001/Burpo.pdf)).

Consequently, a skilled artisan will be able to design an appropriate SGP primer by taking into account the length and sequence of the genomic DNA, and the desired length and specificity of the primer. In one embodiment of the invention, the SGP primer is designed so that it binds with each single-stranded genomic DNA template with a predetermined frequency. In another embodiment of the invention, the SGP primer is designed such that the primer also can act as a forward and reverse primer in the exponential amplification of SGP nucleic acid polymers with a predetermined frequency.

One of skill in the art would also look to the materials and software programs related to other waveform profiling methods and the generation of waveform primers (available from, e.g., Adgene) as an aid in designing primers for SGP (including "universal" primers, and primers for detection of particular species and strains of, e.g., bacteria). However, one of skill would recognize the need to refine the techniques and parameters related to other waveform profiling method for designing primers in order to produce primers that function correctly in SGP. For example, other waveform profiling methods utilize primers that contain both a specific portion and a nonspecific, stabilizing portion (as noted above); the SGP primers of the present invention do not contain a nonspecific stabilizing portion. In addition, one of skill will recognize that it is necessary for the SGP primers to bind to a greater number of binding sites along each single-stranded genomic DNA template (as compared to primers in other waveform profiling methods), at least in part because only a percentage of the SGP nucleic acid polymers will have a sequence comprising the reverse complement of the primer within the preset distance downstream from the primer binding site, i.e., only a percentage will undergo exponential amplification and result in SGP-SGP nucleic acid polymers. Further, only a percentage (e.g., approximately 50%) of SGP-SGP nucleic acid polymers that undergo exponential amplification will produce shortened SGP nucleic acid polymers during a half-time elongation step.

Primers for SGP are designed to be shorter (less bases) than primers used in other waveform profiling methods because the probability that SGP-SGP nucleic acid polymers are produced is increased as the primer length is decreased. For this reason, one of skill in the art would design primers of shorter length than those suggested/recommended for other waveform profiling methods. For example, Adgene presents an example of a waveform primer in a figure (i.e., FIG. 4) of "A Method for Comparison and Identification of DNAs and RNAs by Pattern Analysis: Genopattern Method" (available from Adgene). This waveform primer contains an eleven-base nonspecific stabilizing portion and an eight-base specific portion. One of skill would design primers for SGP by excluding the nonspecific portion, and reducing the number of bases in the total SGP primer to a number less than the number of bases in the specific portion of Adgene's waveform primer. For example, a primer of six or seven bases in length could be designed for use in SGP. In other embodiments in which the specific portion of a particular waveform primer contains more bases, the design for a corresponding SGP primer may, in turn, contain more bases as well.

Among the bacteria that can be detected by the SGP method are those for which universal waveform primers have already been designed; such primers are known in the art and are useful in detecting *Vibrio parahaemolyticus; Pseudomonas aeruginosa; Salmonella typhimurium; Klebsiella pneumoniae; Campylobacter jejuni; Shigella sonnei; Enterococcus faecalis; Haemophilus influenzae; Helicobacter pylori; Streptococcus pyogenes; Mycobacterium bovis; Escherichia coli; Bacillus cereus; Staphylococcus aureus*; and *Bacillus subtilis*. Other primers, several of which can be used to distinguish among individual species and strains of bacteria, are also available from Adgene for use in other waveform profiling methods. As noted above, one of skill would alter the design of the primer, or change the method of designing the primer, in order to produce a primer useful in SGP based on the known waveform primer. In addition, one of skill in the art would design appropriate SGP primers for organisms for which no waveform primer has been designed (for example, for other bacteria and viruses) by analysis of the genomic material of the organism(s) of interest, and by conducting a series of straightforward experimental trials.

One of skill in the art will recognize the applicability of SGP in testing a sample, e.g., a water sample. Methods for isolating organisms, and consequently the genome of the organism, will depend on the sample and are well known in the art. Once potential genomic DNA is isolated, the SGP method may be used to detect the presence of genomic DNA, and thus, the presence of an organism. In certain situations, e.g., when the sample should be sterile or relatively free of contamination, e.g., a water sample, such detection is sufficient to detect contamination by an organism. Where identification of the organism is required, other and more specific SGP primers may be used.

III. Methods of Using the Automated Inline Platform of the Invention

The present invention also provides methods of using an apparatus of the invention for detecting the presence of an organism in a sample, and the subsequent and optional classification of the contaminating organism, i.e., methods of using the microfluidic devices and instruments of the invention to prepare (e.g., isolate, process, mix with reaction reagents), amplify (e.g., by PCR, waveform profiling, etc.) and detect (e.g., screen for, quantify, identify), and/or optionally select for further analysis, (e.g., sequence) genomic material isolated from an organism. Generally, the methods of the invention comprise the steps of 1) aspirating at least one DNA sample droplet into a microfluidic inline reaction channel of a microfluidic device of the invention; 2) forming at least one DNA sample plug by mixing the at least one DNA sample droplet with a primer plug; 3) driving the at least one DNA sample plug along the microfluidic reaction channel into a first temperature-controlled area of the microfluidic device where the DNA sample plug is subjected to at least one amplification cycle comprising denaturing, annealing, and elongation; 4) detecting amplified DNA products in a second temperature-controlled area as the DNA sample plug is subjected to temperatures between a first temperature and a second temperature; and 5) optionally selecting the DNA sample plug for further analysis, e.g., sequencing analysis. The methods described herein will enable one of skill in the art to continuously monitor a sample to screen for contamination even if only a small number of the contaminating organism is present, to quantify the level of any such contamination, and/or to identify the contaminating organism.

A. Amplifying the DNA Sample

As described above, the amplification process occurs within an amplification area, i.e., a first temperature-controlled area of a microfluidic device of the invention. In the first temperature-controlled area of the chip, each microfluidic inline reaction channel is repeatedly and rapidly heated and cooled in a localized manner such that the denaturing, annealing, and elongation steps of the DNA amplification methods, e.g., PCR, waveform profiling, SGP, etc., are effected on each sample plug as it travels along the length of a microfluidic reaction channel. One of skill in the art will recognize that only sample plugs comprising at least one DNA molecule, i.e., DNA sample plugs, will yield amplified DNA products. In one embodiment of the present invention, PCR is chosen as the amplifying process. In another embodiment, waveform profiling is carried out on the automated inline platform disclosed herein. In another embodiment, the waveform profiling method is the SGP method (including but not limited to introduction of the SGP primer, mPCR cycling, formation of higher-order structures, and detection and analysis of amplified shortened SGP nucleic acid polymers), and the SGP waveform profiling method is carried out with the automated inline waveform profiling device disclosed herein.

As such, the invention provides a method of detecting the absence or presence of an organism in a sample, the method comprising, in this order, the steps of: (a) acquiring the sample comprising at least one organism; (b) isolating at least one copy of the genomic material of the organism, if present in the sample; (c) aspirating at least one sample droplet into a microfluidic reaction channel; (d) forming at least one sample plug by mixing the at least one sample droplet with a primer plug, wherein the primer plug comprises at least one primer, nucleotides, DNA polymerase, and intercalators; (e) heating the at least one sample plug to a first temperature that will cause each copy of the DNA to denature into a first and second DNA template; (f) cooling the at least one sample plug to a second temperature to cause the primers to anneal to each genomic DNA template; (g) reheating the at least one sample plug to a third temperature that is between the first and second temperatures as to allow the primers to remain annealed to the genomic DNA and the DNA polymerase to elongate nucleic acid polymers originating from the annealed primers; (h) maintaining the third temperature for a first length of time (i.e., full-time elongation); (i) repeating steps (e)-(h) at least once; and (j) detecting the resulting amplified products, wherein at least steps (c)-(j) occur within an apparatus of the invention. A skilled artisan will recognize that this embodiment effectuates both PCR and waveform amplification methods, depending on the primer or primers chosen. To effectuate a half-time elongation step of the SGP method, the above-described method may be modified to further comprise, after step (i) and before step (j), the steps of (1) repeating steps (e)-(g); (2) maintaining the third temperature for a length of time equal to about 40-60% (preferably about 50%) of the first length of time; and (3) cooling the at least one sample plug to a fourth temperature lower than or equal to that of the second temperature to allow formation of higher-order structures containing intercalators. One of skill in the art will recognize that if the amplification process was PCR, the detecting step of step (j) may occur at one temperature. In contrast, if the waveform profiling was chosen as the amplification process, the detecting step of step (j) should occur at a range of temperatures. As described above, the number of cycles of amplification each sample plug is subject to may be controlled by varying either or both 1) the timing of the voltage applied to the metal tracer, and 2) the flow rate of the sample. The timing of each cycle, and number of cycles of amplification to which each sample plug is subjected, will ultimately depend on the amplification process chosen (e.g., PCR, a waveform profiling method (e.g., the SGP method)), the number of DNA molecules per DNA sample plug, and/or, if PCR is chosen, the length of the DNA region being amplified. The timing of each cycle, and number of cycles for each sample plug tested are experimental conditions that may be determined by a skilled artisan without undue burden. One of skill in the art will recognize that the detecting step described herein may be used to screen for a contaminating organism(s), quantify the level of contamination of a sample, and/or identify the contaminating organism(s). Such detecting methods are described in greater detail below.

B. Detecting the DNA Sample

The detection area of a microfluidic device of the invention allows signals from amplified DNA products to be monitored. Detection may be based on optical, chemical, electrochemical, thermal, or other properties of the amplified DNA products. In one embodiment, detection of signals from amplified DNA products is achieved using an optical detection system, e.g., in the case where amplified DNA products are fluorescent, the detector will typically include a light source that produces light at an appropriate wavelength for activating the fluorescent product, as well as optics for directing the light source through the detection area to products contained in a DNA sample plug within a microfluidic reaction channel.

A skilled artisan will be able to determine the light source needed to detect the amplified DNA products by taking into account, e.g., the appropriate wavelength to excite a fluorescent amplified DNA product. Any light source that provides an appropriate wavelength, including, but not limited to, lasers, laser diodes and LEDs, may be used.

The detection of the fluorescence is accomplished using an appropriate detector, e.g., a photomultiplier tube. The amplified DNA products produced by a method of the invention may be detected by as they pass the detector, e.g., when amplified DNA products need to be detected only at one temperature, e.g., PCR amplified DNA products. Alternatively, the detector may be stationary or may move with the amplified DNA products, e.g., to detect fluorescence as the amplified DNA products are subject to different melting temperatures, e.g., to perform Tm analysis of DNA products amplified by a waveform profiling method, e.g., the SGP method.

In order to detect amplified DNA products, detectable agents must be added to at least those sample plugs comprising DNA. Detectable agents for various forms of detection, e.g., optical, chemical, electrochemical and thermal, are well known in the art. A preferred detectable agent is one that may be detected only in the presence of amplified DNA products. Such detectable agents are well known in the art and include, but are not limited to, fluorescent intercalators. In the methods of the invention, the detectable agent may be added to each sample plug upstream of the detection area (e.g., as a reaction reagent in the preparation of the sample), during amplification of the DNA, just after the sample plug is subject to amplification cycles, etc., as long as the detectable agent is added to a sample plug upstream of the detection area. In the methods of the invention, as the sample plug comprising the detectable agent is moved to the second temperature-controlled area, amplified DNA products (e.g., PCR amplified products, the dissociation of higher-order DNA structures generated by a waveform profiling method in, e.g., the SGP method) may be detected. One of skill in the art will recognize that detection of PCR amplified products may occur at one temperature, whereas detection of the dissociating higher-order structures generated by waveform-profiling methods (including the SGP method) requires at least two different temperatures. The temperature at which PCR amplified products may be detected, e.g., room temperature, depends on the detectable agent that was used. Additionally, detection of the dissociation of higher-order structures generated by waveform profiling methods, e.g., SGP, i.e., melting curve analysis, occurs over a range of temperatures, e.g., 65° C.-95° C., often in the form of a gradient range of temperatures (e.g., applied across a thermal control plate).

One of skill in the art will recognize that the detection step of the methods described herein may be used to screen for contamination, identify the organism responsible for the contamination and/or quantify the level of such contamination. Each of these particular embodiments is described in fuller detail below. Additionally, as mentioned above, an apparatus of the invention may be used to select detected DNA products for further analysis, e.g., sequencing analysis.

1. Screening

It is an object of the invention to provide an inexpensive method for the continuous screening of a sample for contaminating organisms. Screening a sample for the absence or presence of contamination organisms (e.g., detecting the absence or presence of amplified DNA products), i.e., monitoring and keeping public samples, e.g., water and air, free from contaminating organisms and/or terrorist attacks 24 hours a day, 7 days a week and 365 days a year may be an important function of the apparatus of the present invention. Thus, the invention provides the method of using an apparatus of the invention to screen a sample supply for contamination, comprising the steps of continuously acquiring sample droplets from the sample supply into at least one microfluidic reaction channel, forming sample plugs by mixing each sample droplet with a primer plug, wherein each primer plug comprises amplification reagents, amplifying DNA from sample plugs comprising genomic material, and detecting the absence or presence of amplified products, wherein the steps occur in an apparatus of the invention. In this embodiment of the invention, the absence of amplified DNA products (i.e., zero-detection) is indicative of a clean sample supply, e.g., a water supply. In contrast, the presence of amplified products may be indicative of a contaminated sample supply. Using an apparatus of the invention to screen a sample is relatively inexpensive because a large number of tests may be done while avoiding the extraordinary cost in time and money of using conventional methods of screening and monitoring. Additionally, although constant zero-detection may seem redundant, this absence of amplified products indicates that the sample supply is safe. This is an important and vital goal, as is the immediate detection of contamination of the sample supply. Finally, screening for, identifying, and quantifying the level of, a contaminating organism using the methods described herein may be performed simultaneously.

2. Quantifying

In another embodiment of the invention, the apparatus may be used to quantify the level of contamination, i.e., the concentration of genomic material in a sample. The quantification process of the invention using an apparatus of the invention comprises the steps of a) diluting the sample using dilution factors such that the concentration of the genomic material is at most approximately one molecule per sample droplet, e.g., 3 molecules per 1000 sample droplets, b) acquiring sample droplets from the sample into at least one microfluidic inline reaction channel, c) forming sample plugs by mixing each sample droplet with a primer plug, wherein the primer plug comprises amplification reagents, d) subjecting each sample plug to amplification cycles such that each sample plug comprising a DNA molecule has detectable amplified DNA products (and each sample plug not comprising a DNA molecule will not have amplified DNA products), e) detecting the absence or presence of amplified DNA products in each sample plug, and f) determining the ratio of sample plugs containing amplified products to sample plugs resulting in zero-detection, and (g) using the dilution factor to calculate the original concentration of contaminating genomic material in the sample. Quantification using this method is based on the ratio of sample plugs comprising amplified DNA products stemming from one genomic DNA molecule to sample plugs resulting in zero-detection; the method is not based on the fluorescence intensity of the amplified products, and thus, solves a problem inherent with PCR-based quantification schemes.

3. Identifying

The identification method provided herein is only necessary when a sample supply, e.g., a water supply, is contaminated with genomic material that is detected in the screening and/or quantifying method of the invention. Thus, it is another object of the invention to provide an inexpensive method for the identification of an organism in a sample. The invention provides a method of identifying an organism using an apparatus of the invention, the method comprising the steps of a) preparing at least one DNA sample droplet comprising genomic material isolated from the organism; b) acquiring the at least one DNA sample droplet from the sample into at least one microfluidic reaction channel; c) forming at least one DNA sample plug by mixing the at least one sample droplet with a primer plug, wherein the primer plug comprises at least one known first primer; d) subjecting the at least one DNA sample plug to at least one amplification cycle such that the at least one DNA sample plug has detectable amplified DNA products; e) detecting amplified DNA products; f) identifying the organism based on detection of the amplified products, and g) optionally repeating steps (a)-(f) with amplification reagents comprising a known primer that is different than the first known primer to increase the accuracy of the identification of the organism. In one embodiment of the invention, the detection of amplified DNA products (e.g., when samples are being screened for contamination and/or the level of contamination is being quantified) provides the identification of the organism from which the DNA was isolated because the primer was chosen to confirm the identity of an organism, e.g., a specific TAQMAN® primer that specifically binds to the genomic DNA of a particular organism may be chosen such that detection of amplified products using the method(s) described above confirms the identity of the organism. In another embodiment, waveform primers or SGP primers or the invention are used and the detected waveform profile provides the identity of the organism.

In cases when detection of amplified products does not definitively identify the particular species (or strain) of the contaminating organism in a contaminated sample (e.g., during screening or quantifying methods of the invention), the amplified DNA products produced by the initial detection, e.g., in the screening and/or quantifying methods of the invention, may be used as a preliminary indication/suggestion of the type of organism likely to be present in the sample (i.e., the screening or quantification methods may narrow the choices for the primer(s) to use in the optional step of the method of identifying (step g, above)). A library of primers is available for this optional step. Based on the type of organism suggested by the initial detection, one (or more) of these primers may be utilized to produce secondary amplified DNA products, which may then be used to identify the species and strain of organism contaminating the original sample.

In the situation in which more than one source of genomic material is simultaneously contaminating a supply, e.g., a water supply, a variation of the dilution method used for quantification (above) may be employed. Thus, in the case of two contaminating sources of genomic material, by diluting a sample sufficiently to produce a series of sample droplets in which most sample droplets contain no genomic material and some sample droplets contain one or the other genomic material, the array of possible components in each sample droplet or subsequent sample plug may be represented as: 0 (no DNA); X (one genomic DNA source); and Y (a second genomic DNA source). One of ordinary skill in the art would understand that such a dilution scheme would normally isolate one molecule of genomic material per sample droplet, if any. However, in the rare instance in which two different DNA molecules are present in a single sample plug (e.g., XY), the method would still be useful; for example, the waveform profile for the presence of both organisms (i.e., XY) would not have a normal waveform profile for any singular bacterial source.

One of skill in the art will readily recognize that by monitoring a series of these sample plugs (e.g., one thousand sample plugs), the detection and identification of sample plugs containing genomic material from each separate source may be obtained. For example, in the SGP method, the use of an SGP primer will detect waveform profiles for sample plugs that contain (1) genomic DNA for organism X and (2) genomic DNA for organism Y. To further identify the X and Y organisms, in one embodiment, the sample plugs corresponding to these organisms are isolated and are selected for further analysis, e.g., selected for analysis by a DNA sequencing chip by means of the valve device of the invention. One of ordinary skill in the art also would know to expand and extrapolate this variation on the methods related to the device of the invention to situations in which more than two sources of genomic material contamination are present. One of skill in the art would recognize that these methods for identifying multiple sources of genomic material would also be useful for detecting and discriminating a dangerous source of contamination against a background of an innocuous, or relatively innocuous, source of contamination in a supply, e.g., a water supply.

4. Selecting

Using an apparatus of the invention provides another benefit in the analysis of genomic material; an apparatus of the invention allows for the selection of amplified DNA products for further analysis, e.g., sequencing analysis. Sequencing analysis is a final and definitive method of DNA analysis. As such, it is another object of the invention to provide a method of using an apparatus of the invention to provide detailed information, e.g., sequence information, regarding DNA that has been analyzed using any of the methods described above. Consequently, the invention provides a method in which a DNA sample plug that has traversed the length of a microfluidic inline reaction channel within a microfluidic device of the invention may be optionally selected for further analysis. The selection process will occur at the "valve" of a microfluidic device of the invention. Upon selection, the valve of the microfluidic device of the invention will further allow the selected DNA sample plug(s) to proceed to another device, e.g., for sequencing, e.g., a DNA sequencing chip. Such chips are known in the art (see, e.g., U.S. Published Patent Application No. 2005/0009022).

The entire contents of all references, patents, and patent applications cited throughout the present application are hereby incorporated by reference herein in their entireties.

EXAMPLES

Embodiments of the invention are discussed herein. The basis of one embodiment of the invention, i.e., the basis of a system for detecting the absence or presence of a contaminating organism in a sample, is found in Example 1. One of skill in the art will recognize the utility of such a system in providing quality assurance for various samples, e.g., for detecting the absence or presence of bacteria in a water supply. Again, it will be recognized by one of skill in the art that the present invention may be used to analyze the absence or presence of genes and other lengths of nucleotides in different samples. For example, one of skill in the art could use the present invention to detect and identify anthrax in a sample filtered from an air supply or in a sample of blood, or detect and identify a virus coated on various foodstuffs. The present invention should not be construed to be limited to the scope of the specific examples described below.

Example 1

Figure 3A:
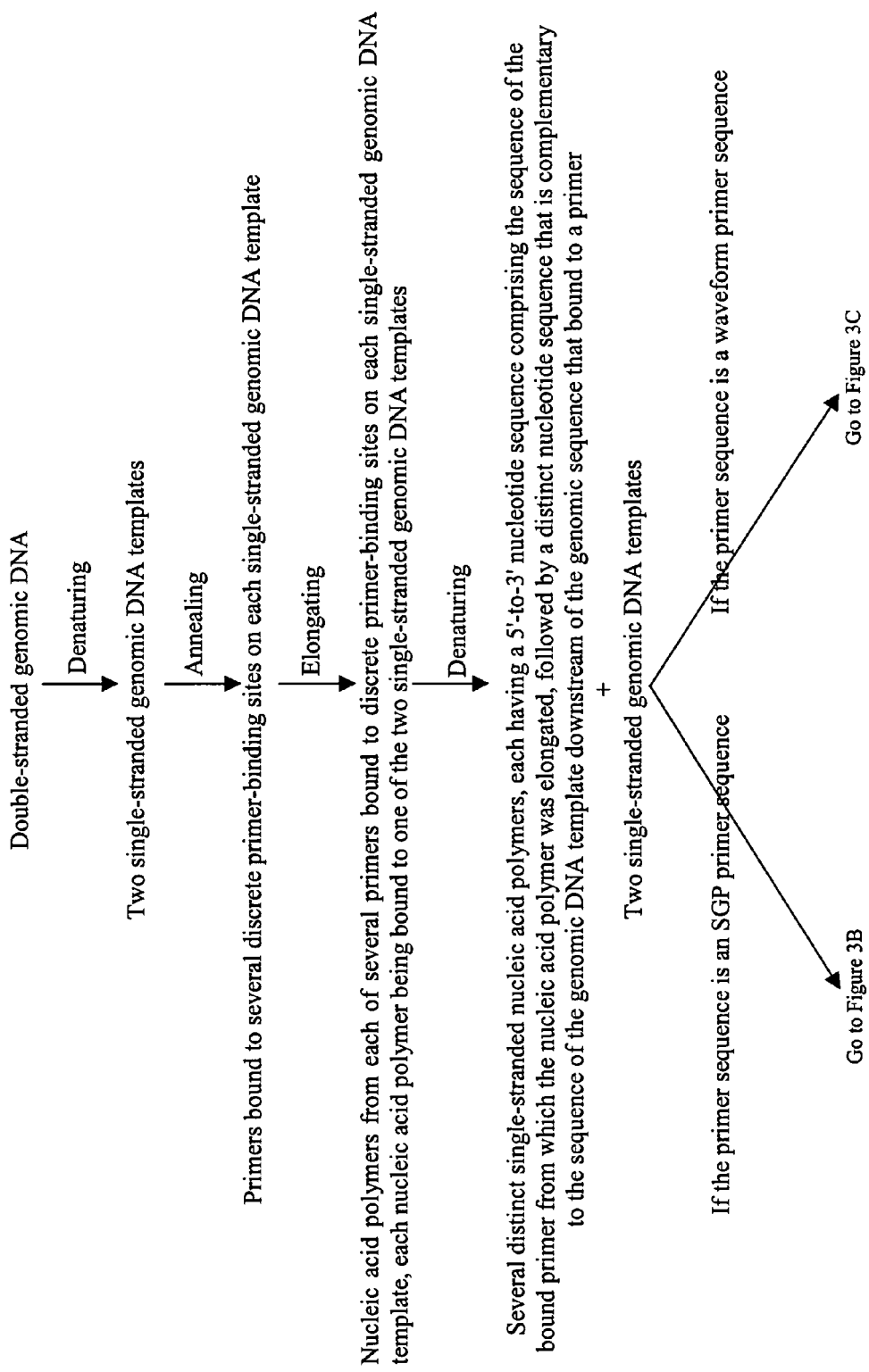
FIG. 3: Flow diagram (FIGS. 3A, 3B, and 3C) delineating the steps of, and nucleic acid polymers resulting from, a waveform profiling method and Single Genome Profiling method.
Figure 3B:
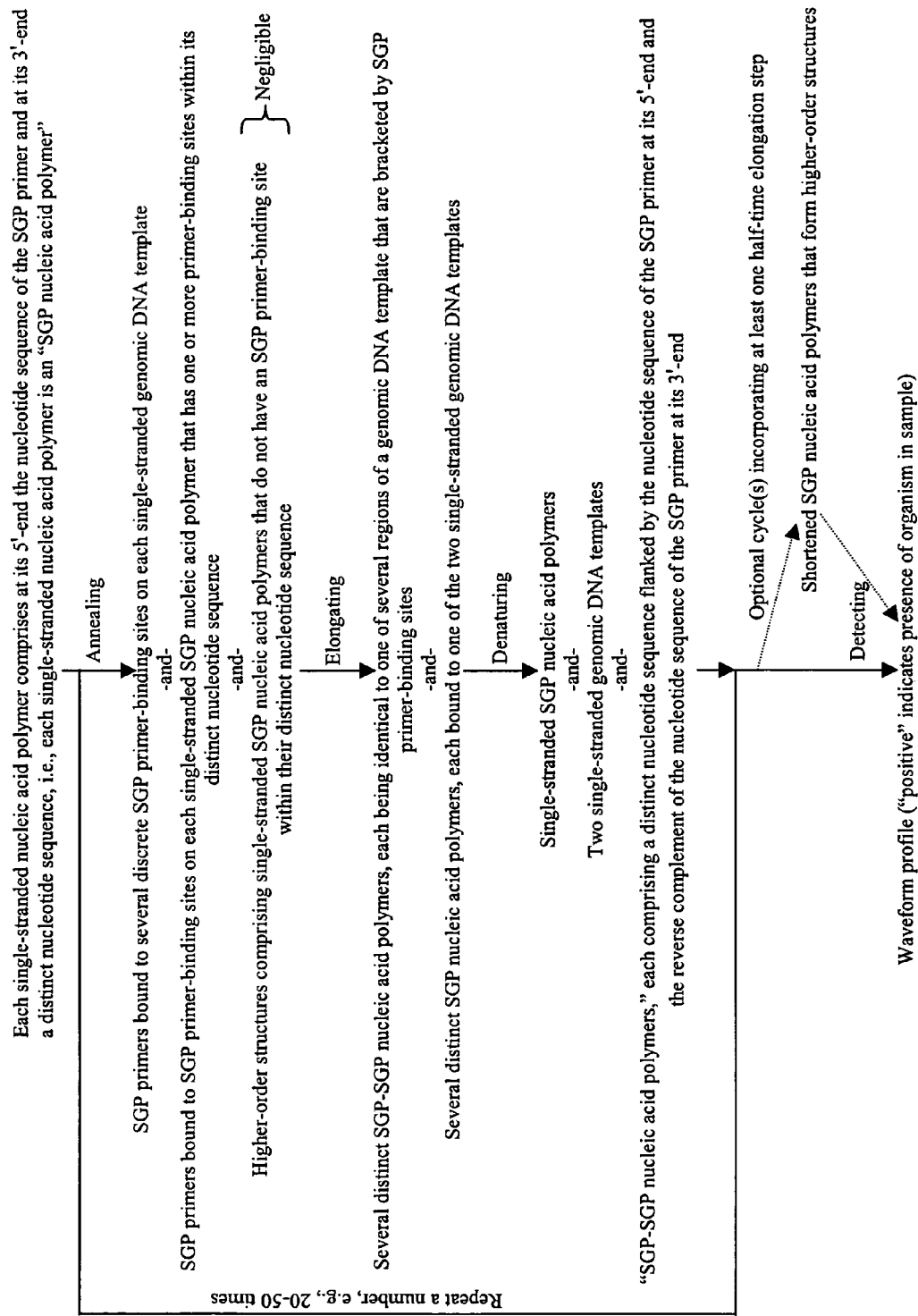
Figure 3C:
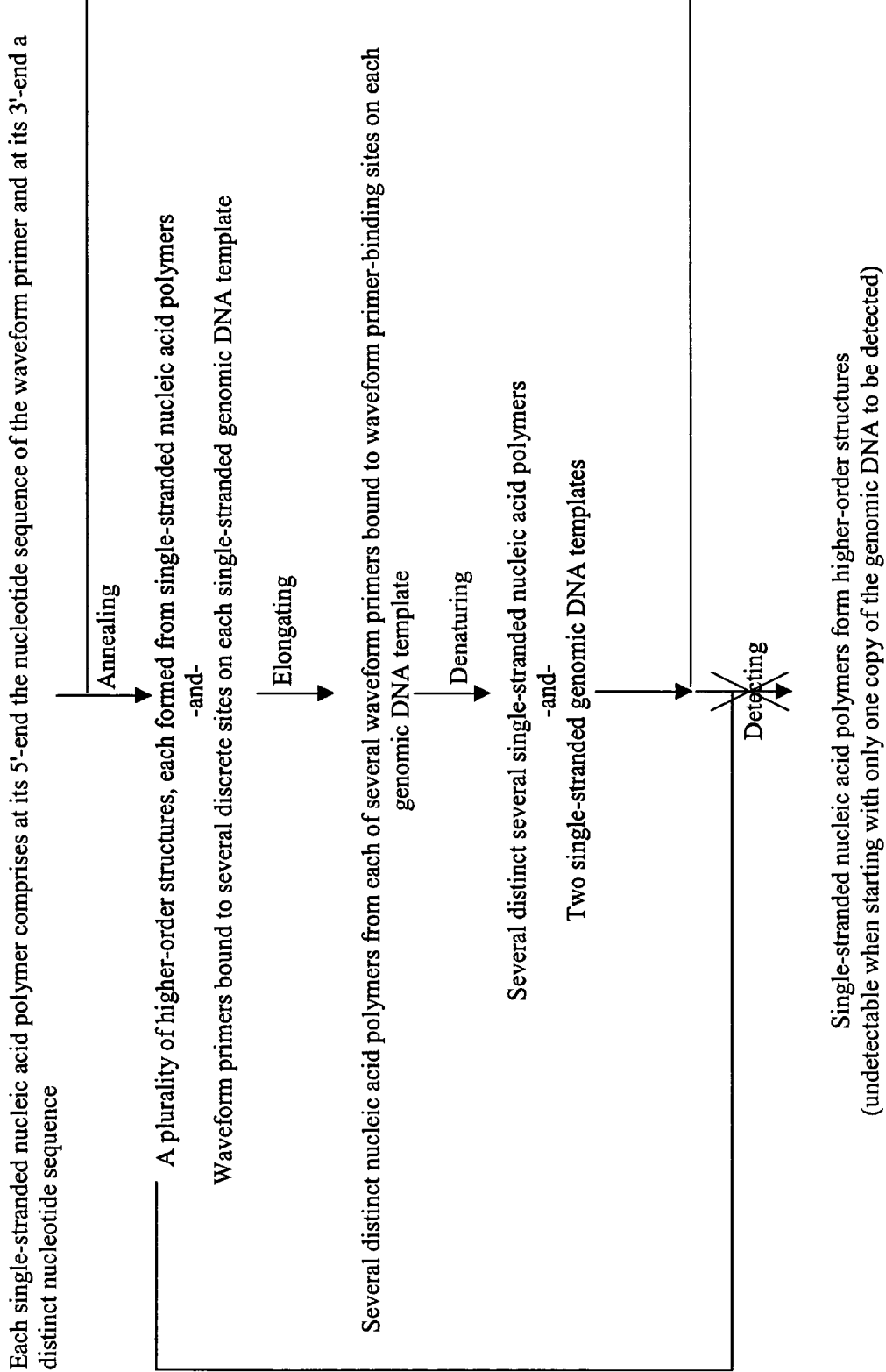

The Single Genome Profile (SGP) Method Comprising Modified PCR (mPCR) and Half-Time Elongation Step The examples and figures provided herein are theoretical constructions provided to aid one of skill in the art in an understanding of the invention, as well as to delineate the improvements described herein. FIG. 3 is a flow diagram that delineates the first cycle of waveform profiling methods, including the SGP method (FIG. 3A), and compares the results of subsequent cycles of the SGP method (FIG. 3B) and other waveform profiling methods (FIG. 3C). It should be noted that the flow diagram represents the use of one copy of the genomic DNA to be detected. However, as discussed above, only with the SGP method will this amount of genomic DNA be sufficient for the formation of detectable higher-order structures.

To further demonstrate the invention, both a theoretical primer sequence and a theoretical genomic sequence are provided in Example 1.1 and Example 1.2, respectively, to demonstrate how a primer of sufficiently short length will be able to bind to several discrete primer binding sites along the length of each single-stranded genomic DNA template. Example 1.3 then guides one of skill in the art through the SGP process described herein, provides the sequences of each nucleic acid polymer expected after each step of the SGP method, and helps to delineate the improvements of the invention. The examples presented herein should not be construed or understood as limiting the scope of the invention.

Example 1.1

Theoretical Primer Sequence

In the model provided herein, the primer is 5'-AGC-3'.

Example 1.2

Theoretical Genomic Sequence

A 1001 bp genomic sequence containing the four DNA nucleotide bases (adenine "A," guanine "G," thymidine "T," and cytosine "C") in random order and frequency was generated by use of a computer program. A few bases of this theoretical, randomly generated sequence were altered in order to obtain a sequence that more clearly demonstrates the SGP method. The sequence of each of the single-stranded genomic DNA templates of the double-stranded genomic DNA is shown in FIG. 4. The sequence of one of the single-stranded genomic DNA templates is presented 5'-to-3' and is represented by uppercase letters corresponding to the nucleotide bases (SEQ ID NO:1); the complementary single-stranded genomic DNA template is presented 3'-to 5' and is represented by lowercase letters corresponding to the nucleotide bases (SEQ ID NO:2). Bolded letters on each genomic DNA template show the sites at which the theoretical primer of Example 1.1 is expected to anneal, i.e., primer binding sites. The bracketed regions in FIG. 4 demonstrate the several discrete regions of the theoretical genomic DNA that are bracketed by primer binding sites, each of which will be exponentially amplified in the form of SGP-SGP nucleic acid polymers (see, e.g., FIG. 7).

Example 1.3

SGP Method Comprising Modified PCR and a Half-Time Elongation Step

The primer of Example 1.1 is expected to anneal to each primer-binding site along the genomic DNA of Example 1.2. The first cycle of mPCR begins with denaturing the genomic DNA into two genomic DNA templates, which is performed at ~95-98° C. for approximately 2 minutes. Denaturing is followed by annealing of the primer to several discrete complementary sites, i.e., primer binding sites, on each single-stranded genomic DNA template. Annealing occurs at ~25° C. for approximately 2 minutes. After the primer has annealed to several discrete complementary sites on each single-stranded genomic DNA template, a polymerase, e.g., Taq polymerase, elongates distinct nucleic acid polymers, i.e., SGP nucleic acid polymers, starting at the 3' end of the primer and extending in 5' to 3' direction. Elongation occurs at ~72° C. for approximately 2 minutes, and as such, in this theoretical first cycle of mPCR, SGP nucleic acid polymers of ~21 bases or less are produced.

Figure 5A:
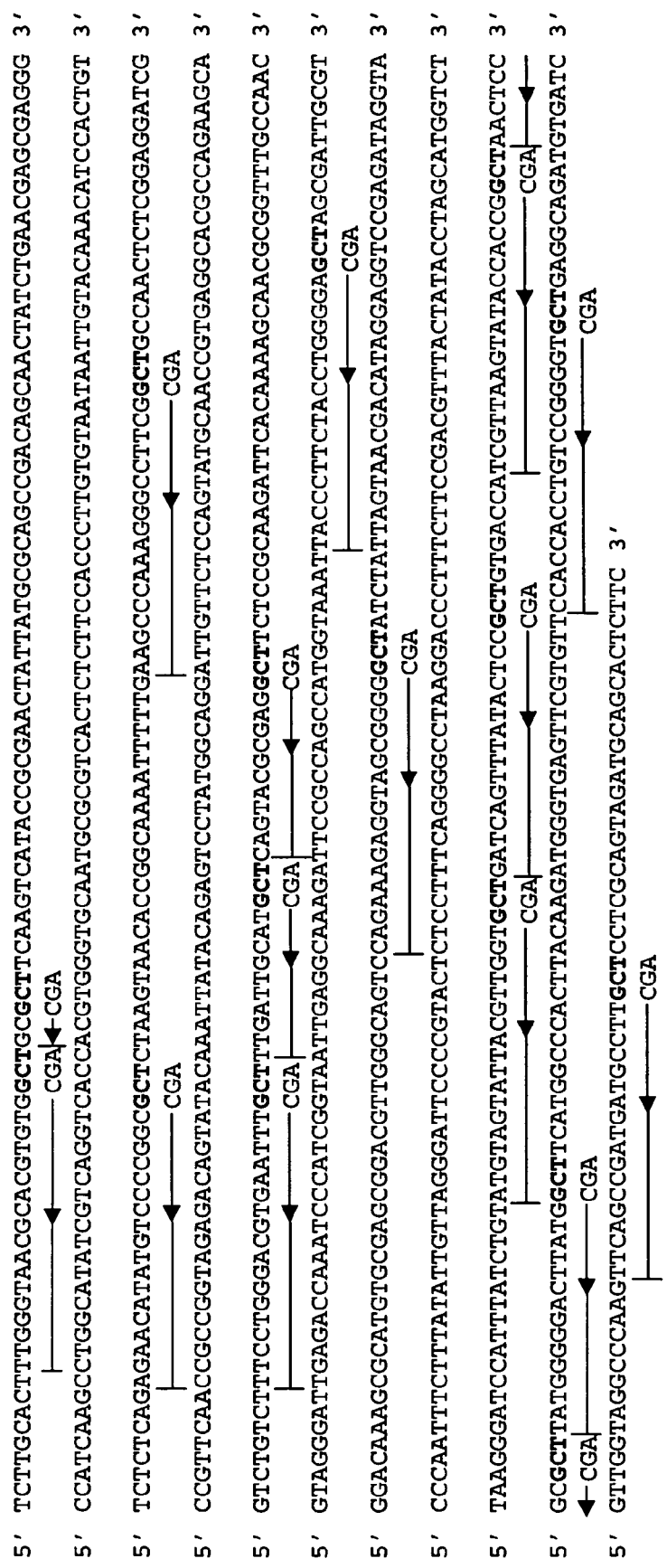
FIG. 5: The genomic DNA of FIG. 4 depicted denatured into two single-stranded genomic DNA templates (FIGS. 5A and 5B), with the theoretical primer annealed to primer binding sites on each of the denatured single-stranded genomic DNA templates, and arrows depicting regions of each genomic DNA from which SGP nucleic acid polymers will be derived.
Figure 5B:
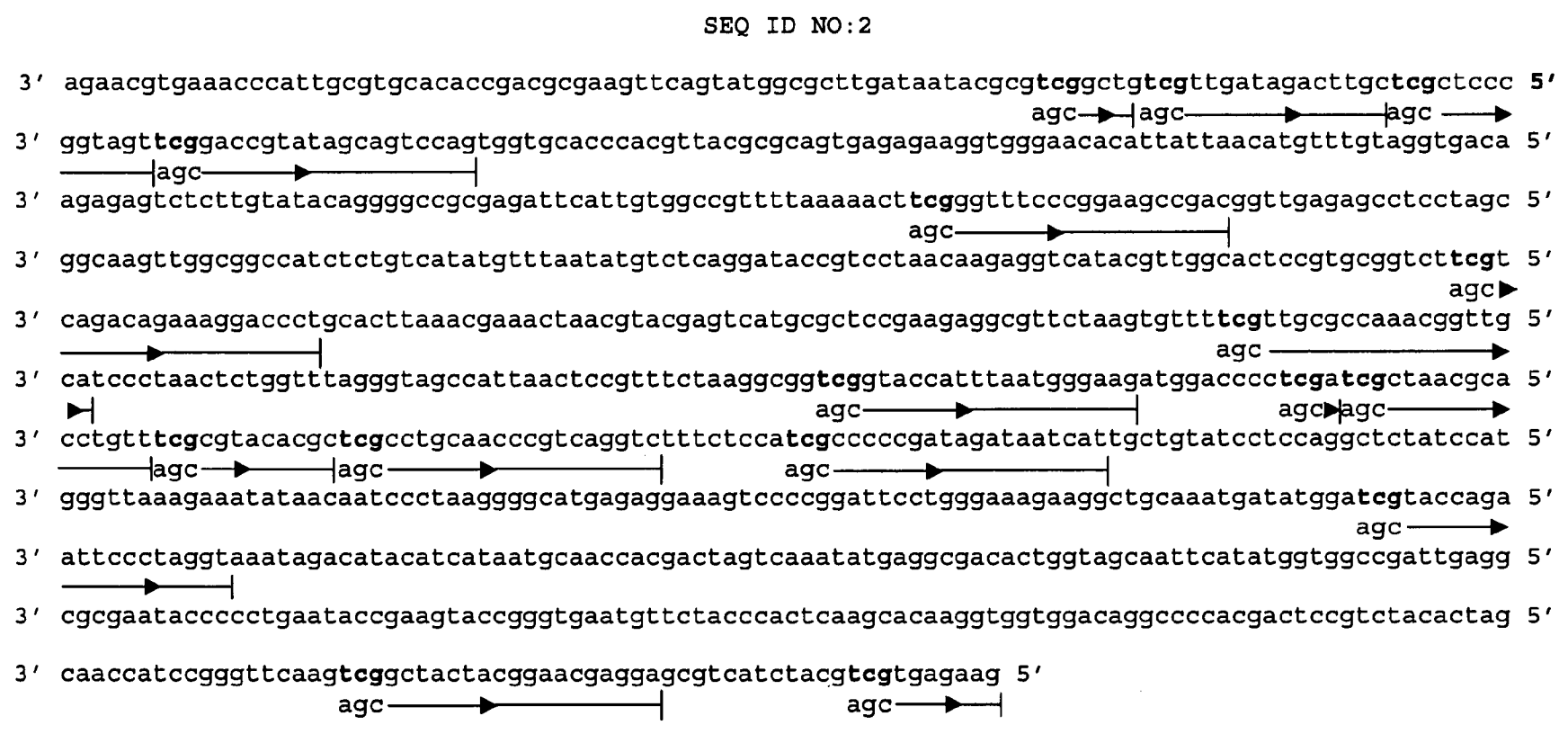

A representation of the first cycle of mPCR with the theoretical primer and genomic DNA sequences of Examples 1.1 and 1.2 is represented in FIGS. 5 and 6. FIG. 5 shows the theoretical genomic DNA sequence (also depicted in FIG. 4) as two denatured single-stranded DNA templates. The sequence of one of the single-stranded DNA templates is depicted 5'-to-3' and by uppercase letters (FIG. 5A; SEQ ID NO:1), and the sequence of the complementary single-stranded DNA template is depicted 3'-to-5' and by lowercase letters (FIG. 5B; SEQ ID NO:2). Also, bold letters indicate the expected primer annealing sites. The regions of the genomic DNA the SGP nucleic acid polymers are expected to be derived from during the first cycle of amplification are represented underneath each genomic DNA template by 1) letters corresponding to the theoretical primer sequence underneath each primer binding site to depict binding of the primer to the primer binding site, 2) an arrow depicting the direction of elongation of the SGP nucleic acid polymer, and 3) a cross-hatch demonstrating the expected length of the elongated SGP nucleic acid polymer. Sequences of SGP nucleic acid polymers that are expected to be generated from each genomic DNA template after the first cycle of amplification are listed in FIG. 6 (SEQ ID NOs:3-34). As shown, the sequences of some SGP nucleic acid polymers comprise SGP primer binding sites (represented by bolded sequences).

During the denaturing step of the second, and subsequent, cycles of amplification, the SGP nucleic acid polymers having sequences comprising SGP primer binding sites (as shown in FIG. 6) will be separated from each genomic DNA template, and will participate in subsequent annealing and elongation steps, i.e., they will not form higher-order structures. Consequently, in second and subsequent amplification cycles, in addition to the SGP nucleic acid polymers set forth in FIG. 6, a set of SGP-SGP nucleic acid polymers set forth in FIG. 7 (SEQ ID NOs:35-42) will be synthesized and amplified.

One of skill in the art will readily recognize that each of the sequences set forth in FIG. 7, i.e., each SGP-SGP nucleic acid polymer sequence, is identical to one of the several regions of a genomic DNA template bracketed by primer binding sites (as depicted with brackets in FIG. 4), i.e., is bracketed by the SGP primer sequence and the reverse complement of the SGP primer sequence. One of skill in the art will also recognize that subsequent cycles of amplification will result in an exponential doubling of the sequences listed in FIG. 7. It is approximated that after 22-24 cycles, approximately $10^6$ to $10^7$ copies of each distinct SGP-SGP nucleic acid polymer listed in FIG. 7 will be generated from one copy of the genome.

A "half-time" elongation step is included after several, e.g., 22-24, mPCR cycles containing full-time elongation steps, such that the 3' end of some of the SGP-SGP nucleic acid polymers listed in FIG. 7 will not be copied because the elongation time is reduced. The "half-time" elongation step will be approximately 40-60% of the length of time used in the previous full-time elongation steps, for example, 50% of the length of time of the elongation step used above.

In the present example, elongation during the half-time step occurs at ~72° C. for approximately 1 minute. Such a time for elongation allows the polymerization of ~10 base pairs. As such, only a nucleic acid polymer derived from an SGP-SGP nucleic acid polymer that has one of the following sequences (as listed in FIG. 7) will be fully elongated such that it will comprise a primer-binding site: 3'-tcga-5' (set forth as SEQ ID NO:36), 3'-tcgccccga-5' (set forth as SEQ ID NO:37), 5'-AGCT-3' (set forth as SEQ ID NO:40), or 5'-AGCGGGGGCT-3' (set forth as SEQ ID NO:41). Such SGP-SGP nucleic acid polymers will not participate in the formation of higher order structures.

In contrast, a nucleic acid polymer copied in a half-time elongation step from an SGP-SGP nucleic acid polymer having one of the following sequences (as listed in FIG. 7) will be a shortened SGP nucleic acid polymer, i.e., it will not have a sequence comprising a primer-binding site: 3'-tcgggtttcccg-gaagccga-5' (set forth as SEQ ID NO:35), 3'-tcggctactacg-gaacga-5' (set forth as SEQ ID NO:38), 5'-AGC-CCAAAGGGCCTTCGGCT-3' (set forth as SEQ ID NO:39), or 5'-AGCCGATGATGCCTTGCT-3' (set forth as SEQ ID NO:42). The sequences of SGP-SGP nucleic acid polymers and shortened SGP nucleic acid polymers expected to be derived from the SGP-SGP nucleic acid polymers listed in FIG. 7 after a half-time elongation step are listed in FIG. 8. The shortened SGP nucleic acid polymers, i.e., those that do not have an SGP primer-binding site and will participate in the formation of higher-order structures, are underlined in FIG. 8 and have sequences as follows: 5'-AGCCCAAAGG-3' (set forth as SEQ ID NO:43), 5'-AGCCGATGAT-3' (set forth as SEQ ID NO:46), 3'-cggaagccga-5' (set forth as SEQ ID NO:47) and 3'-tacggaacga-5' (set forth as SEQ ID NO:50).

The subsequent mPCR cycles including a half-time elongation step in place of the full-time elongation step result in single-stranded shortened SGP nucleic acid polymers that will not have complementary strands, thus they will form higher-order structures. These higher-order structures can be detected by performing Tm analysis (waveform profiling). In contrast, shorter SGP-SGP nucleic acid polymers, e.g., 5'-AGCT-3', will be completely elongated during mPCR with a half-time elongation step. Thus, because a complete complementary SGP-SGP nucleic acid polymer will always form during the half-time elongation step, these shorter SGP-SGP nucleic acid polymers will bind to their complementary nucleic acid polymer and will not participate in the formation of higher order structures.

What is claimed is:

1. A method of detecting the absence or presence of one or more organisms in one or more samples, comprising the steps of:
- (a) providing a microfluidic device comprising a microfluidic reagent assembly area which forms two or more sample plugs, said microfluidic reagent assembly area being in fluid communication with at least one microfluidic inline channel that runs through an amplification area and a detection area, said microfluidic reagent assembly area comprising:
  - i. a sample droplet forming area which receives one or more samples containing the same or different genomic material and forms one or more samples into said one or more sample droplets, said sample droplet forming area comprises a sample droplet microfluidic path in fluid communication with said microfluidic inline channel which forwards the one or more sample droplets to said microfluidic inline channel;
  - ii. a primer plug producing area comprising a primer assembly apparatus which assembles one or more primer plugs comprising amplification reagents including at least one primer, wherein said primer assembly apparatus is controlled to assemble said one or more primer plugs containing the same primers or different primers, said primer plug producing area further comprises a primer plug microfluidic path in fluid communication with said microfluidic inline channel which forwards the one or more primer plugs to the microfluidic inline channel; and
  - iii. a sample plug mixing area which forms sample plugs by mixing said sample droplet and primer plug, said sample plug mixing area being in fluid communication with the microfluidic inline channel;
  wherein said microfluidic reagent assembly area is controlled to form sample plugs that comprise the same or different genomic material and the same or different primers;
- (b) acquiring samples that may contain an organism;
- (c) selecting one or more samples to input into said sample droplet forming area of the device;
- (d) isolating at least one copy of the genomic material if present from each of the selected samples in the sample droplet forming area;
- (e) introducing at least one sample droplet of each of the selected samples into the microfluidic inline channel through the sample droplet microfluidic path;
- (f) driving the sample droplets along the microfluidic inline channel through the reagent assembly area;
- (g) selecting two or more primer plugs to input into the primer plug microfluidic path of the device;
- (h) assembling the selected primer plugs in the primer plug assembly area, wherein each primer plug comprises amplification reagents and at least one primer, and wherein the primer plugs contain the same primers or different primers;
- (i) introducing the primer plugs into the microfluidic inline channel through the primer plug microfluidic path;
- (j) forming two or more sample plugs in the microfluidic inline channel by mixing the sample droplets with the primer plugs in the microfluidic inline channel in the sample plug mixing area, wherein the sample plugs comprise the same or different genomic material and the same or different primers;
- (k) driving the sample plugs along the microfluidic inline channel through the amplification area;
- (l) amplifying the genomic material, if present, in each of the sample plugs in the microfluidic inline channel in the amplification area of the device;
- (m) driving the sample plugs along the microfluidic inline channel through the detection area; and
- (n) detecting the absence or presence of amplified products in each of the sample plugs,
wherein the presence of amplified products for an organism is indicative of the presence of the organism in the sample.

2. The method of claim 1, wherein the at least one primer comprises a PCR primer pair.

3. The method of claim 1, wherein the at least one primer comprises a waveform profiling primer or a single genome profiling (SGP) primer.

4. The method of claim 1, wherein the detecting step of step (n) occurs at one temperature.

5. The method of claim 1, wherein the detecting step of step (n) occurs at a range of temperatures.

6. The method of claim 1, wherein the amplification reagents comprise nucleotides, DNA polymerase, magnesium and a buffer.

7. The method of claim 6, wherein the amplification reagents further comprise a detection agent.

8. The method of claim 1, wherein multiple sample droplets from one or more samples are introduced into the microfluidic inline channel of the device.

9. The method of claim 8, wherein the multiple sample droplets are from one sample.

10. The method of claim 8, wherein primer plugs containing different primers are mixed with the multiple sample droplets to form multiple sample plugs in the microfluidic inline reaction channel of the device.

11. The method of claim 10, wherein the different primers are capable of amplifying genomic material of different organisms.

12. The method of claim 8, wherein the multiple sample droplets are from two or more samples.

13. The method of claim 12, wherein primer plugs containing the same primers are mixed with the multiple sample droplets to form multiple sample plugs in the microfluidic inline reaction channel of the device.

14. The method of claim 12, wherein primer plugs containing different primers are mixed with the multiple sample droplets to form multiple sample plugs in the microfluidic inline reaction channel of the device.

15. The method of claim 14, wherein the different primers are capable of amplifying genomic material of different organisms.

16. The method of claim 1, wherein the one or more samples are from a sample supply that is continuously selected and wherein the presence of an organism in the sample indicates contamination of the sample supply.

17. The method of claim 1, which further comprises identifying the one or more organisms on the basis of the amplified products and the primers used to amplify the sample plugs.

18. The method of claim 1, wherein the sample droplet forming area further comprises a genomic isolation area comprising a filtering apparatus, a genomic material isolation apparatus and a genomic material concentration adjusting apparatus.

19. A method of detecting the absence or presence of an organism in a sample comprising the steps of:
  (a) providing a microfluidic device comprising a microfluidic reagent assembly area which forms two or more sample plugs, said microfluidic reagent assembly area being in fluid communication with at least one microfluidic inline channel that runs through an amplification area and a detection area, said microfluidic reagent assembly area comprising:
    i. a sample droplet forming area which receives one or more samples containing the same or different genomic material and forms one or more samples into said one or more sample droplets, said sample droplet forming area comprises a sample droplet microfluidic path in fluid communication with said microfluidic inline channel which forwards the one or more sample droplets to said microfluidic inline channel;
    ii. a primer plug producing area comprising a primer assembly apparatus which assembles one or more primer plugs comprising amplification reagents including at least one primer, wherein said primer assembly apparatus is controlled to assemble said one or more primer plugs containing the same primers or different primers, said primer plug producing area further comprises a primer plug microfluidic path in fluid communication with said microfluidic inline channel which forwards the one or more primer plugs to the microfluidic inline channel; and
    iii. a sample plug mixing area which forms sample plugs by mixing said sample droplet and primer plug, said sample plug mixing area being in fluid communication with the microfluidic inline channel;
  wherein said microfluidic reagent assembly area is controlled to form sample plugs that comprise the same or different genomic material and the same or different primers; and
  wherein the microfluidic device further comprising at least one microfluidic inline channel that runs through (i) an amplification area within a first temperature-controlled area and (ii) a detection area within a second temperature-controlled area, wherein the at least one microfluidic inline channel comprises a valve downstream of the detection area through which a sample selectively flows and wherein the device controls fluid movement within the microfluidic inline channel, heating and cooling of the first and second temperature-controlled areas and data acquisition from the microfluidic device;
  (b) acquiring a sample that may contain an organism;
  (c) isolating at least one copy of the genomic material of the organism, if present in the sample, in the reagent assembly area of the micro fluidic device;
  (d) introducing at least one sample droplet into one microfluidic inline reaction channel;
  (e) driving the at least one sample droplet along the microfluidic inline channel through the reagent assembly area;
  (f) forming at least one sample plug by mixing the at least one sample droplet with at least one primer plug in the microfluidic inline channel in the reagent assembly area of the device, wherein each primer plug comprises amplification reagents and at least one primer, and wherein the primer plugs contain the same or different primers;
  (g) driving the at least one sample plug along the microfluidic inline channel through the amplification area;
  (h) amplifying the genomic material, if present, in the at least one sample plug in the microfluidic inline channel in the amplification area of the device;
  (i) driving the at least one sample plug along the microfluidic inline channel through the detection area;
  (j) detecting the absence or presence of amplified products in the microfluidic inline channel in the detection area of the device to produce a detection result, wherein the presence of the amplified products is indicative of the presence of the organism;
  (k) selecting the sample plug for further analysis or waste removal on the basis of the detection result;
  (l) driving the at least one sample plug along the microfluidic inline channel to a valve; and
  (m) directing flow of the sample plug through the valve in the microfluidic inline channel on the basis of the selection in step (k).

20. The method of claim 19, wherein the valve selectively switches fluid flow within the at least one microfluidic inline reaction channel from a first direction to a second direction based on data collected for the selection in step (k).

21. The method of claim 19, wherein the at least one primer comprises a PCR primer pair.

22. The method of claim 19, wherein the at least one primer comprises a waveform profiling primer or a single genome profiling (SGP) primer.

23. The method of claim 19, wherein the detecting step of step (j) occurs at one temperature.

24. The method of claim 19, wherein the detecting step of step (j) occurs at a range of temperatures.

25. The method of claim 19, wherein the amplification reagents further comprise a detection agent.

26. The method of claim 19, wherein the sample is from a sample supply that is continuously monitored at a predetermined interval and wherein the presence of an organism in the sample indicates contamination of the sample supply.

27. The method of claim 19, which further comprises identifying the organism on the basis of the amplified products and the primers used to amplify the sample plugs.

28. A method of detecting the presence or absence of genomic material in two or more samples, comprising the steps of:
- (a) providing a microfluidic device comprising a microfluidic reagent assembly area which forms two or more sample plugs, said microfluidic reagent assembly area being in fluid communication with at least one microfluidic inline channel that runs through an amplification area and a detection area, said microfluidic reagent assembly area comprising:
  - i. a sample droplet forming area which receives one or more samples containing the same or different genomic material and forms one or more samples into said one or more sample droplets, said sample droplet forming area comprises a sample droplet microfluidic path in fluid communication with said microfluidic inline channel which forwards the one or more sample droplets to said microfluidic inline channel;
  - ii. a primer plug producing area comprising a primer assembly apparatus which assembles one or more primer plugs comprising amplification reagents including at least one primer, wherein said primer assembly apparatus is controlled to assemble said one or more primer plugs containing the same primers or different primers, said primer plug producing area further comprises a primer plug microfluidic path in fluid communication with said microfluidic inline channel which forwards the one or more primer plugs to the microfluidic inline channel; and
  - iii. a sample plug mixing area which forms sample plugs by mixing said sample droplet and primer plug, said sample plug mixing area being in fluid communication with the microfluidic inline channel;

wherein said microfluidic reagent assembly area is controlled to form sample plugs that comprise the same or different genomic material and the same or different primers;
- (b) selecting two or more samples for detecting the presence or absence of the genomic material in each of said samples;
- (c) introducing one or more sample droplets of each of the selected samples into the microfluidic inline channel of the microfluidic device, wherein each sample droplet contains genomic material if present;
- (d) selecting two or more primer plugs to input into said microfluidic inline channel, wherein each primer plug comprises amplification reagents and at least one primer, wherein the primer plugs contain the same primers or different primers based on the selection of the primer plugs and wherein the primers are selected on the basis of the genomic material to be detected;
- (e) forming two or more sample plugs in said microfluidic inline channel by mixing the sample droplets with the primer plugs in the microfluidic inline channel, wherein the sample plugs comprise the same or different genomic material and the same or different primers;
- (f) amplifying the genomic material in the sample plugs in said microfluidic inline channel to produce amplified products if genomic material is present in the sample plugs; and
- (g) detecting the presence or absence of the resulting amplified products in each of the sample plugs, wherein the presence of amplified products in a sample plug is indicative of the presence of the genomic material in the sample.

29. The method of claim 28, which further comprises the step of:
- (g) identifying the genomic material in the sample plug, wherein the genomic material is identified on the basis of the amplified products and the primer plugs selected for forming the sample plugs.

30. The method of claim 28, wherein the at least one primer comprises a PCR primer pair.

31. The method of claim 28, wherein the at least one primer comprises a waveform profiling primer or a single genome profiling (SGP) primer.

32. The microfluidic device of claim 28, wherein the amplification reagents comprise nucleotides, DNA polymerase, magnesium and a buffer.

33. The microfluidic device of claim 32, wherein the selected amplification reagents further comprise a detectable agent.

34. The method of claim 28, wherein the two or more samples are from a sample supply that is continuously selected and wherein the presence of an organism in the sample indicates contamination of the sample supply.

* * * * *

SEQUENCE LISTING

<160> NUMBER OF SEQ ID NOS: 50

<210> SEQ ID NO 1
<211> LENGTH: 1001
<212> TYPE: DNA
<213> ORGANISM: Artificial
<220> FEATURE:
<223> OTHER INFORMATION: Theoretical single-strand DNA template

<400> SEQUENCE: 1

```
tcttgcactt tgggtaacgc acgtgtggct gcgcttcaag tcataccgcg aactattatg      60
cgcagccgac agcaactatc tgaacgagcg agggccatca agcctggcat atcgtcaggt     120
caccacgtgg gtgcaatgcg cgtcactctc ttccacccct gtgtaataat tgtacaaaca     180
tccactgttc tctcagagaa catatgtccc cggcgctcta agtaacaccg gcaaaatttt     240
tgaagcccaa agggccttcg gctgccaact ctcggaggat cgccgttcaa ccgccggtag     300
agacagtata caaattatac agagtcctat ggcaggattg ttctccagta tgcaaccgtg     360
aggcacgcca gaagcagtct gtctttcctg ggacgtgaat ttgctttgat tgcatgctca     420
gtacgcgagg cttctccgca agattcacaa aagcaacgcg gtttgccaac gtagggattg     480
agaccaaatc ccatcggtaa ttgaggcaaa gattccgcca gccatggtaa attacccttc     540
tacctgggga gctagcgatt gcgtggacaa agcgcatgtg cgagcggacg ttgggcagtc     600
cagaaagagg tagcggggc tatctattag taacgacata ggaggtccga gataggtacc     660
caatttcttt atattgttag ggattccccg tactctcctt tcagggcct  aaggacccct     720 tcttccgacg tttactatac ctagcatggt cttaagggat ccatttatct gtatgtagta     780
ttacgttggt gctgatcagt ttatactccg ctgtgaccat cgttaagtat accaccggct     840
aactccgcgc ttatggggga cttatggctt catgccccac ttacaagatg ggtgagttcg     900
tgttccacca cctgtccggg gtgctgaggc agatgtgatc gttggtaggc ccaagttcag     960
ccgatgatgc cttgctcctc gcagtagatg cagcactctt c                       1001
```

<210> SEQ ID NO 2
<211> LENGTH: 1001
<212> TYPE: DNA
<213> ORGANISM: Artificial
<220> FEATURE:
<223> OTHER INFORMATION: Theoretical single-strand DNA template
<220> FEATURE:
<221> NAME/KEY: misc_feature
<223> OTHER INFORMATION: This sequence is in 3' to 5' direction.

<400> SEQUENCE: 2

```
agaacgtgaa acccattgcg tgcacaccga cgcgaagttc agtatggcgc ttgataatac      60
```

```
gcgtcggctg tcgttgatag acttgctcgc tcccggtagt tcggaccgta tagcagtcca    120
gtggtgcacc cacgttacgc gcagtgagag aaggtgggaa cacattatta acatgtttgt    180
aggtgacaag agagtctctt gtatacaggg gccgcgagat tcattgtggc cgttttaaaa    240
acttcgggtt tcccggaagc cgacggttga gagcctccta gcggcaagtt ggcggccatc    300
tctgtcatat gtttaatatg tctcaggata ccgtcctaac aagaggtcat acgttggcac    360
tccgtgcggt cttcgtcaga cagaaaggac cctgcactta aacgaaacta acgtacgagt    420
catgcgctcc gaagaggcgt tctaagtgtt ttcgttgcgc caaacggttg catccctaac    480
tctggtttag ggtagccatt aactccgttt ctaaggcggt cggtaccatt taatgggaag    540
atggacccct cgatcgctaa cgcacctgtt tcgcgtacac gctcgcctgc aacccgtcag    600
gtctttctcc atcgccccg atagataatc attgctgtat cctccaggct ctatccatgg     660
gttaaagaaa tataacaatc cctaaggggc atgagaggaa agtccccgga ttcctgggaa    720
agaaggctgc aaatgatatg gatcgtacca gaattcccta ggtaaataga catacatcat    780
aatgcaacca cgactagtca aatatgaggc gacactggta gcaattcata tggtggccga    840
ttgaggcgcg aataccccct gaataccgaa gtaccgggtg aatgttctac ccactcaagc    900
acaaggtggt ggacaggccc cacgactccg tctacactag caaccatccg ggttcaagtc    960
ggctactacg gaacgaggag cgtcatctac gtcgtgagaa g                        1001
```

<210> SEQ ID NO 3
<211> LENGTH: 7
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 3 agccgac                                                               7

<210> SEQ ID NO 4
<211> LENGTH: 16
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 4
agcaactatc tgaacg                                                     16

<210> SEQ ID NO 5
<211> LENGTH: 14
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 5
agcgagggcc atca                                                       14

<210> SEQ ID NO 6
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:2

-continued

```
<400> SEQUENCE: 6
agcctggcat atcgtcaggt c                                                21

<210> SEQ ID NO 7
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 7
agcccaaagg gccttcggct g                                                21

<210> SEQ ID NO 8
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 8
agcagtctgt ctttcctggg a                                                21

<210> SEQ ID NO 9
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 9
agcaacgcgg tttgccaacg t                                                21

<210> SEQ ID NO 10
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 10
agccatggta aattaccctt c                                                21

<210> SEQ ID NO 11
<211> LENGTH: 4
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 11 agct                                                                    4

<210> SEQ ID NO 12
<211> LENGTH: 17
<212> TYPE: DNA
<213> ORGANISM: Artificial
<220> FEATURE:
<223> OTHER INFORMATION: SGP nucleic acid polymer derived from SEQ ID
      NO:2
```

```
<400> SEQUENCE: 12
agcgattgcg tggacaa                                                    17

<210> SEQ ID NO 13
<211> LENGTH: 12
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 13
agcgcatgtg cg                                                         12

<210> SEQ ID NO 14
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 14
agcggacgtt gggcagtcca g                                               21

<210> SEQ ID NO 15
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 15
agcgggggct atctattagt a                                               21

<210> SEQ ID NO 16
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 16
agcatggtct taagggatcc a                                               21

<210> SEQ ID NO 17
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 17
agccgatgat gccttgctcc t                                               21

<210> SEQ ID NO 18
<211> LENGTH: 10
<212> TYPE: DNA
<213> ORGANISM: Artificial
<220> FEATURE:
<223> OTHER INFORMATION: SGP nucleic acid polymer derived from SEQ ID
      NO:2

<400> SEQUENCE: 18
```

-continued agcactcttc                                                          10

<210> SEQ ID NO 19
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 19
aacccattgc gtgcacaccg a                                             21

<210> SEQ ID NO 20
<211> LENGTH: 5
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 20 cgcga                                                                5

<210> SEQ ID NO 21
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 21
tcttgtatac aggggccgcg a                                             21

<210> SEQ ID NO 22
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 22
ttcgggtttc ccggaagccg a                                             21

<210> SEQ ID NO 23
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 23
aaggaccctg cacttaaacg a                                          21

<210> SEQ ID NO 24
<211> LENGTH: 13
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 24
aactaacgta cga                                                   13

<210> SEQ ID NO 25
<211> LENGTH: 14
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 25
gtcatgcgct ccga                                                  14

<210> SEQ ID NO 26
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 26
atgggaagat ggacccctcg a                                          21

<210> SEQ ID NO 27
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 27
gtctttctcc atcgccccg a                                           21

<210> SEQ ID NO 28
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

```
<400> SEQUENCE: 28
tacatcataa tgcaaccacg a                                              21

<210> SEQ ID NO 29
<211> LENGTH: 19
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 29
ctagtcaaat atgaggcga                                                 19

<210> SEQ ID NO 30
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 30
agcaattcat atggtggccg a                                              21

<210> SEQ ID NO 31
<211> LENGTH: 11
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 31
ttgaggcgcg a                                                         11

<210> SEQ ID NO 32
<211> LENGTH: 18
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 32 atacccctg aataccga                                                   18

<210> SEQ ID NO 33
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
```

<223> OTHER INFORMATION: This sequence is in 3' to 5' direction.

<400> SEQUENCE: 33
ggtggtggac aggccccacg a                                              21

<210> SEQ ID NO 34
<211> LENGTH: 21
<212> TYPE: DNA
<213> ORGANISM: Artificial
<220> FEATURE:
<223> OTHER INFORMATION: SGP nucleic acid polymer derived from SEQ ID
      NO:1
<220> FEATURE:
<221> NAME/KEY: misc_feature
<223> OTHER INFORMATION: This sequence is in 3' to 5' direction.

<400> SEQUENCE: 34
aagtcggcta ctacggaacg a                                              21

<210> SEQ ID NO 35
<211> LENGTH: 20
<212> TYPE: DNA
<213> ORGANISM: Artificial
<220> FEATURE:
<223> OTHER INFORMATION: SGP-SGP nucleic acid polymer derived from SEQ
      ID NO:2
<220> FEATURE:
<221> NAME/KEY: misc_feature
<223> OTHER INFORMATION: This sequence is in 3' to 5' direction.

<400> SEQUENCE: 35
tcgggtttcc cggaagccga                                                20

<210> SEQ ID NO 36
<211> LENGTH: 4
<212> TYPE: DNA
<213> ORGANISM: Artificial
<220> FEATURE:
<223> OTHER INFORMATION: SGP-SGP nucleic acid polymer derived from SEQ
      ID NO:2
<220> FEATURE:
<221> NAME/KEY: misc_feature
<223> OTHER INFORMATION: This sequence is in 3' to 5' direction.

<400> SEQUENCE: 36 tcga                                                                  4

<210> SEQ ID NO 37
<211> LENGTH: 10
<212> TYPE: DNA
<213> ORGANISM: Artificial
<220> FEATURE:
<223> OTHER INFORMATION: SGP-SGP nucleic acid polymer derived from SEQ
      ID NO:2
<220> FEATURE:
<221> NAME/KEY: misc_feature
<223> OTHER INFORMATION: This sequence is in 3' to 5' direction.

<400> SEQUENCE: 37
tcgccccga                                                            10

<210> SEQ ID NO 38
<211> LENGTH: 18
<212> TYPE: DNA
<213> ORGANISM: Artificial
<220> FEATURE:
<223> OTHER INFORMATION: SGP-SGP nucleic acid polymer derived from SEQ
      ID NO:2
<220> FEATURE:

```
<221> NAME/KEY: misc_feature
<223> OTHER INFORMATION: This sequence is in 3' to 5' direction.

<400> SEQUENCE: 38
tcggctacta cggaacga                                                           18

<210> SEQ ID NO 39
<211> LENGTH: 20
<212> TYPE: DNA
<213> ORGANISM: Artificial
<220> FEATURE:
<223> OTHER INFORMATION: SGP-SGP nucleic acid polymer derived from SEQ
      ID NO:1

<400> SEQUENCE: 39
agcccaaagg gccttcggct                                                         20

<210> SEQ ID NO 40
<211> LENGTH: 4
<212> TYPE: DNA
<213> ORGANISM: Artificial
<220> FEATURE:
<223> OTHER INFORMATION: SGP-SGP nucleic acid polymer derived from SEQ
      ID NO:1

<400> SEQUENCE: 40 agct                                                                           4

<210> SEQ ID NO 41
<211> LENGTH: 10
<212> TYPE: DNA
<213> ORGANISM: Artificial
<220> FEATURE:
<223> OTHER INFORMATION: SGP-SGP nucleic acid polymer derived from SEQ
      ID NO:1

<400> SEQUENCE: 41 agcggggggct                                                                   10

<210> SEQ ID NO 42
<211> LENGTH: 18
<212> TYPE: DNA
<213> ORGANISM: Artificial
<220> FEATURE:
<223> OTHER INFORMATION: SGP-SGP nucleic acid polymer derived from SEQ
      ID NO:1

<400> SEQUENCE: 42
agccgatgat gccttgct                                                           18

<210> SEQ ID NO 43
<211> LENGTH: 10
<212> TYPE: DNA
<213> ORGANISM: Artificial
<220> FEATURE:
<223> OTHER INFORMATION: shortened SGP nucleic acid polymer derived from
      SEQ ID NO:2

<400> SEQUENCE: 43
agcccaaagg                                                                    10

<210> SEQ ID NO 44
<211> LENGTH: 4
<212> TYPE: DNA
<213> ORGANISM: Artificial
<220> FEATURE:
<223> OTHER INFORMATION: SGP-SGP nucleic acid polymer derived from SEQ
```

```
         ID NO:2

<400> SEQUENCE: 44 agct                                                                    4

<210> SEQ ID NO 45
<211> LENGTH: 10
<212> TYPE: DNA
<213> ORGANISM: Artificial
<220> FEATURE:
<223> OTHER INFORMATION: SGP-SGP nucleic acid polymer derived from SEQ
      ID NO:2

<400> SEQUENCE: 45
agcgggggct                                                             10

<210> SEQ ID NO 46
<211> LENGTH: 10
<212> TYPE: DNA
<213> ORGANISM: Artificial
<220> FEATURE:
<223> OTHER INFORMATION: Shortened SGP nucleic acid polymer derived from
      SEQ ID NO:2

<400> SEQUENCE: 46
agccgatgat                                                             10

<210> SEQ ID NO 47
<211> LENGTH: 10
<212> TYPE: DNA
<213> ORGANISM: Artificial
<220> FEATURE:
<223> OTHER INFORMATION: Shortened SGP nucleic acid polymer derived from
      SEQ ID NO:1
<220> FEATURE:
<221> NAME/KEY: misc_feature
<223> OTHER INFORMATION: This sequence is in 3' to 5' direction.

<400> SEQUENCE: 47
cggaagccga                                                             10

<210> SEQ ID NO 48
<211> LENGTH: 4
<212> TYPE: DNA
<213> ORGANISM: Artificial
<220> FEATURE:
<223> OTHER INFORMATION: SGP-SGP nucleic acid polymer derived from SEQ
      ID NO:1
<220> FEATURE:
<221> NAME/KEY: misc_feature
<223> OTHER INFORMATION: This sequence is in 3' to 5' direction.

<400> SEQUENCE: 48 tcga                                                                    4

<210> SEQ ID NO 49
<211> LENGTH: 10
<212> TYPE: DNA
<213> ORGANISM: Artificial
<220> FEATURE:
<223> OTHER INFORMATION: SGP-SGP nucleic acid polymer derived from SEQ
      ID NO:1
<220> FEATURE:
<221> NAME/KEY: misc_feature
<223> OTHER INFORMATION: This sequence is in 3' to 5' direction.

<400> SEQUENCE: 49
tcgcccccga                                                             10
```

```
<210> SEQ ID NO 50
<211> LENGTH: 10
<212> TYPE: DNA
<213> ORGANISM: Artificial
<220> FEATURE:
<223> OTHER INFORMATION: Shortened SGP nucleic acid polymer derived from
      SEQ ID NO:1
<220> FEATURE:
<221> NAME/KEY: misc_feature
<223> OTHER INFORMATION: This sequence is in 3' to 5' direction.

<400> SEQUENCE: 50
tacggaacga                                                              10
```